US010674893B2

United States Patent
Nakada et al.

(10) Patent No.: US 10,674,893 B2
(45) Date of Patent: Jun. 9, 2020

(54) ENDOSCOPIC SURGICAL DEVICE AND GUIDE DEVICE

(71) Applicant: FUJIFILM Corporation, Tokyo (JP)

(72) Inventors: Kimiaki Nakada, Kanagawa (JP); Takumi Dejima, Kanagawa (JP); Masayuki Iwasaka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/883,102

(22) Filed: Jan. 30, 2018

(65) Prior Publication Data

US 2018/0153379 A1 Jun. 7, 2018

Related U.S. Application Data

(63) Continuation of application No. PCT/JP2016/069921, filed on Jul. 5, 2016.

(30) Foreign Application Priority Data

Jul. 30, 2015 (JP) .................................. 2015-150826

(51) Int. Cl.
*A61B 1/00* (2006.01)
*A61B 17/34* (2006.01)
(Continued)

(52) U.S. Cl.
CPC ............ *A61B 1/00128* (2013.01); *A61B 1/00* (2013.01); *A61B 1/00087* (2013.01);
(Continued)

(58) Field of Classification Search
None
See application file for complete search history.

(56) References Cited

U.S. PATENT DOCUMENTS

| 4,538,594 A | 9/1985 | Boebel et al. |
| 2005/0119525 A1* | 6/2005 | Takemoto .......... A61B 1/00154 600/114 |

(Continued)

FOREIGN PATENT DOCUMENTS

| JP | 2002-330928 | 11/2002 |
| JP | 2011-528576 | 11/2011 |

(Continued)

OTHER PUBLICATIONS

"Notice of Allowance of Japan Counterpart Application", with English translation thereof, dated Aug. 3, 2018, p. 1-p. 6.

(Continued)

*Primary Examiner* — Aaron B Fairchild
(74) *Attorney, Agent, or Firm* — JCIPRNET

(57) ABSTRACT

An overtube, which is punctured into a body wall and guides an endoscope and a treatment tool into a body cavity, includes an interlocking member that interlocks the forward and backward movements of the endoscope and the treatment tool with each other. The interlocking member is constituted of a first sleeve coupled to the endoscope, a second sleeve coupled to the treatment tool, and a coupling member having an elastic body, which couples the first sleeve and the second sleeve together. Accordingly, in a case where the stretching of the coupling member is small, the endoscope interlocks with the forward and backward movement of the treatment tool at a slow response, and in a case where the stretching of the coupling member is large, the endoscope interlock with the forward and backward movement of a treatment tool at a quick response.

18 Claims, 24 Drawing Sheets

(51) Int. Cl.
*A61B 17/29* (2006.01)
*A61B 1/06* (2006.01)

(52) U.S. Cl.
CPC ...... *A61B 1/00154* (2013.01); *A61B 17/3421* (2013.01); *A61B 1/06* (2013.01); *A61B 2017/2906* (2013.01); *A61B 2017/3445* (2013.01)

(56) References Cited

U.S. PATENT DOCUMENTS

| | | |
|---|---|---|
| 2010/0016659 A1 | 1/2010 | Weitzner |
| 2010/0105983 A1 | 4/2010 | Oneda et al. |
| 2011/0230713 A1 | 9/2011 | Kleemann et al. |
| 2015/0080650 A1 | 3/2015 | Dejima et al. |
| 2016/0174825 A1 | 6/2016 | Dejima |
| 2016/0174826 A1 | 6/2016 | Dejima |

FOREIGN PATENT DOCUMENTS

| | | |
|---|---|---|
| JP | 2012-501695 | 1/2012 |
| WO | 2013176167 | 11/2013 |
| WO | 2015033908 | 3/2015 |
| WO | 2015033909 | 3/2015 |

OTHER PUBLICATIONS

"International Search Report (Form PCT/ISA/210) of PCT/JP2016/069921", with English translation thereof, dated Oct. 4, 2016, pp. 1-4.
"Written Opinion (Form PCT/ISA/237)", dated Oct. 4, 2016, with English translation thereof, pp. 1-7.

* cited by examiner

ENDOSCOPIC SURGICAL DEVICE AND GUIDE DEVICE

CROSS-REFERENCE TO RELATED APPLICATIONS

This application is a Continuation of PCT International Application No. PCT/JP2016/069921 filed on Jul. 5, 2016, which claims priority under 35 U.S.C. § 119(a) to Japanese Patent Application No. 2015-150826 filed on Jul. 30, 2015. Each of the above applications is hereby expressly incorporated by reference, in their entirety, into the present application.

BACKGROUND OF THE INVENTION

1. Field of the Invention

The present invention relates to an endoscopic surgical device and a guide device, and particularly, to an endoscopic surgical device and a guide device that interlock an endoscope and a treatment tool with each other.

2. Description of the Related Art

A laparoscope is known as an endoscope instrument to be inserted into an abdominal cavity from the body surface skin. Surgery (laparoscopic surgery) using this laparoscope has been prevalent in may surgeries in recent years because a surgical wound is smaller compared to abdominal surgery, open-chest surgery, or the like and a bedtime period after surgery be shortened.

Generally, in the laparoscopic surgery (for example, laparoscopic gallbladder removal surgery or the like), a surgeon who performs a treatment and an endoscopic technician who performs the operation of the laparoscope are present, and treatment and the operation of the laparoscope are separately performed. For this reason, during surgery, the surgeon performs the treatment while serially gives instructions to the endoscopic technician such that an optimal image for performing the treatment is obtained.

However, in a system in which the surgeon gives instructions to the endoscopic technician, there is a problem that it is difficult to obtain an image the surgeon desires truly and the surgeon is stressed. Additionally, since the endoscopic technician operates after a surgeon gives an instruction, there is also a problem that the operation takes substantial time. Moreover, since a surgeon's hand and an endoscopic technician's hand may interfere with each other on a patient's abdominal wall, there is also a problem that the operation becomes complicated.

In contrast, the applicant of the present application has suggested a technique of interlocking an endoscope and a treatment tool in a state where the endoscope and the treatment tool are inserted into an overtube (for example, refer to WO2015/033909A).

According to this technique, since the endoscope moves forward and backward with play with respect to the forward and backward movement of the treatment tool, it is possible to prevent the size of a target to be observed from fluctuating unnecessarily in a case where the treatment tool is minutely displaced in the axial direction, a sense of perspective can be suitably maintained, and a stable observation image can be provided.

Additionally, in a case where the treatment tool is largely displaced in the axial direction, the range of an observation image that is obtained by the endoscope in an interlocking manner with the large displacement is changed. Thus, the size of a target to be observed changes according to the operation of the treatment tool, and it is possible for the surgeon to simply obtain a desired image, and the operability is improved.

Hence, the surgeon can easily obtain a desired image with a simple operation without increasing a burden on the surgeon.

SUMMARY OF THE INVENTION

Meanwhile, in the overtube, cost reduction and simplification of the configuration are major issues. Particularly, it is desired that the function of interlocking the endoscope and the treatment tool with each other is satisfied and cost reduction and simplification of the configuration is achieved.

The invention has been made in view of such circumstances, and an object thereof is to provide an endoscopic surgical device and a guide device that can satisfy the function of interlocking two medical instruments with each other in an overtube and can achieve cost reduction and simplification of the configuration.

In order to achieve the above object, an endoscopic surgical device according to an aspect of the invention comprises a first medical instrument having a first insertion part; a second medical instrument having a second insertion part; a tubular overtube allowing the first insertion part and the second insertion part to be inserted therethrough and guiding the first insertion part and the second insertion part into a body cavity; a first holding part that is disposed inside the overtube, holds the first insertion part inserted through the inside of the overtube, and moves in an axial direction of the overtube in a state where the first insertion part is held; a second holding part that is disposed inside the overtube, holds the second insertion part inserted through the inside of the overtube, and moves in the axial direction of the overtube in a state where the second insertion part is held; a coupling member which has a first fixing part fixed to the first holding part and a second fixing part fixed to the second holding part, and has an elastic body between the first fixing part and the second fixing part; and a resistance force generating part that generates a resistance force which hinders the movement of the first holding part in the axial direction of the overtube.

According to the present aspect, since the two medical instruments can be inserted into the body cavity via one overtube, and a body wall can be punctured in one site. Therefore, low-invasive (a burden on the body is little) surgery can be performed.

Additionally, since the first holding part holding the first medical instrument and the second holding part holding the second medical instrument are coupled together by the coupling member having the elastic body, the first medical instrument and the second medical instrument can be operated in an interlocking manner with the response being delayed.

Accordingly, one surgeon can simultaneously perform the forward and backward movement operation of the two medical instruments with his/her single hand, and unnecessary follow-up of one medical instrument with respect to axial minute displacement (a small amplitude of forward and backward movement operation) of the other medical instrument can be prevented. For example, in a case where the first medical instrument is an endoscope, the visual field (imaging region) of the endoscope can be made to follow a treatment portion in the second medical instrument, and the surgeon can always be provided with an optimal image for treatment (the surgeon can display a desired image without stress). Meanwhile, since the endoscope does not respond temporarily and is not unnecessarily displaced with respect to the axial minute displacement of the second medical instrument, a screen for an image captured by the endoscope can be prevented from shaking, and it is possible to provide an image that is easy for the surgeon to see.

Additionally, since a configuration for interlocking the first holding part and the second holding part with each other is a simple configuration in which the first holding part and the second holding part are coupled together by the coupling member having the elastic body, cost reduction and simplification of the configuration can be achieved.

In the endoscopic surgical device related to still another aspect of the invention, it is possible to adopt an aspect in which, in a case where a natural length between the first fixing part and the second fixing part of the coupling member is defined as L1 and a distance between the first fixing part and the second fixing part when the second fixing part has moved relative to the overtube is defined as L2, the coupling member generates a force of biasing the first fixing part and the second fixing part in a direction in which the first fixing part and the second fixing part are brought close to each other in the axial direction of the overtube, in a case where the distance L2 becomes longer than L1.

In the endoscopic surgical device related to still another aspect of the invention, it is possible to adopt an aspect in which, in the coupling member, the force of biasing the first fixing part and the second fixing part in the direction in which the fixing parts are brought close to each other in the axial direction of the overtube becomes larger as the distance of L2 becomes longer than L1.

In the endoscopic surgical device related to a still further aspect of the invention, it is possible to adopt an aspect in which, in a case where a natural length between the first fixing part and the second fixing part of the coupling member is defined as L1 and a distance between the first fixing part and the second fixing part when the second fixing part has moved relative to the overtube is defined as L2, the coupling member generates a force of biasing the first fixing part and the second fixing part in a direction in which the first fixing part and the second fixing part are moved away from each other in the axial direction of the overtube, in a case where the distance L2 becomes shorter than L1.

In the endoscopic surgical device related to a still further aspect of the invention, it is possible to adopt an aspect in which, in the coupling member, the force of biasing the first holding part and the second holding part in the direction in which the first holding part and the second holding part are moved away from each other in the axial direction of the overtube becomes larger as the distance of L2 becomes shorter than L1.

In the endoscopic surgical device related to a still further aspect of the invention, it is possible to adopt an aspect in which the resistance force generating part is provided between the first holding part and the overtube.

In the endoscopic surgical device related to a still further aspect of the invention, it is possible to adopt an aspect in which the resistance force generating part is provided between the first insertion part and the overtube.

In the endoscopic surgical device related to a still further aspect of the invention, it is possible to adopt an aspect in which the overtube has a valve member that secures the airtightness in an internal space of the overtube by being in contact with the first insertion part, and the resistance force generating part is provided between the first holding part and the valve member.

In the endoscopic surgical device related to a still further aspect of the invention, it is possible to adopt an aspect in which the first medical instrument is an endoscope in which an observation part is provided at a distal end of the first insertion part, and the second medical instrument is a treatment tool in which a treatment part is provided at a distal end of the second insertion part.

Additionally, in order to achieve the above object, a guide device according to a still further aspect of the invention comprises a tubular overtube allowing a first insertion part of a first medical instrument and a second insertion part of a second medical instrument to be inserted therethrough and guiding the first insertion part and the second insertion part into a body cavity; a first holding part that is disposed inside the overtube, holds the first insertion part inserted through the inside of the overtube, and moves in an axial direction of the overtube in a state where the first insertion part is held; a second holding part that is disposed inside the overtube, holds the second insertion part inserted through the inside of the overtube, and moves in the axial direction of the overtube in a state where the second insertion part is held; a coupling member which has a first fixing part fixed to the first holding part and a second fixing part fixed to the second holding part, and has an elastic body between the first fixing part and the second fixing part; and a resistance force generating part that generates a resistance force which hinders the movement of the first holding part in the axial direction of the overtube.

According to the present aspect, since the two medical instruments can be inserted into the body cavity via one overtube, and a body wall can be punctured in one site. Therefore, low-invasive (a burden on the body is little) surgery can be performed.

Additionally, since the first holding part holding the first medical instrument and the second holding part holding the second medical instrument are coupled together by the coupling member having the elastic body, the first medical instrument and the second medical instrument can be operated in an interlocking manner with the response being delayed.

Accordingly, one surgeon can simultaneously perform the forward and backward movement operation of the two medical instruments with his/her single hand, and unnecessary follow-up of one medical instrument with respect to axial minute displacement (a small amplitude of forward and backward movement operation) of the other medical instrument can be prevented. For example, in a case where the first medical instrument is an endoscope, the visual field (imaging region) of the endoscope can be made to follow a treatment portion in the second medical instrument, and the surgeon can always be provided with an optimal image for treatment (the surgeon can display a desired image without stress). Meanwhile, since the endoscope does not respond temporarily and is not unnecessarily displaced with respect to the axial minute displacement of the second medical instrument, a screen for an image captured by the endoscope can be prevented from shaking, and it is possible to provide an image that is easy for the surgeon to see.

Additionally, since a configuration for interlocking the first holding part and the second holding part with each other is a simple configuration in which the first holding part and the second holding part are coupled together by the coupling member having the elastic body, cost reduction and simplification of the configuration can be achieved.

According to the invention, the function of interlocking two medical instruments with each other in an overtube can be satisfied and cost reduction and simplification of the configuration can be achieved.

DESCRIPTION OF THE PREFERRED EMBODIMENTS

Preferred embodiments of the invention will be described below in detail according to the accompanying drawings. In addition, any of the drawings may illustrate main parts in an exaggerated manner for description, and may have dimensions different from actual dimensions.

Figure 1:
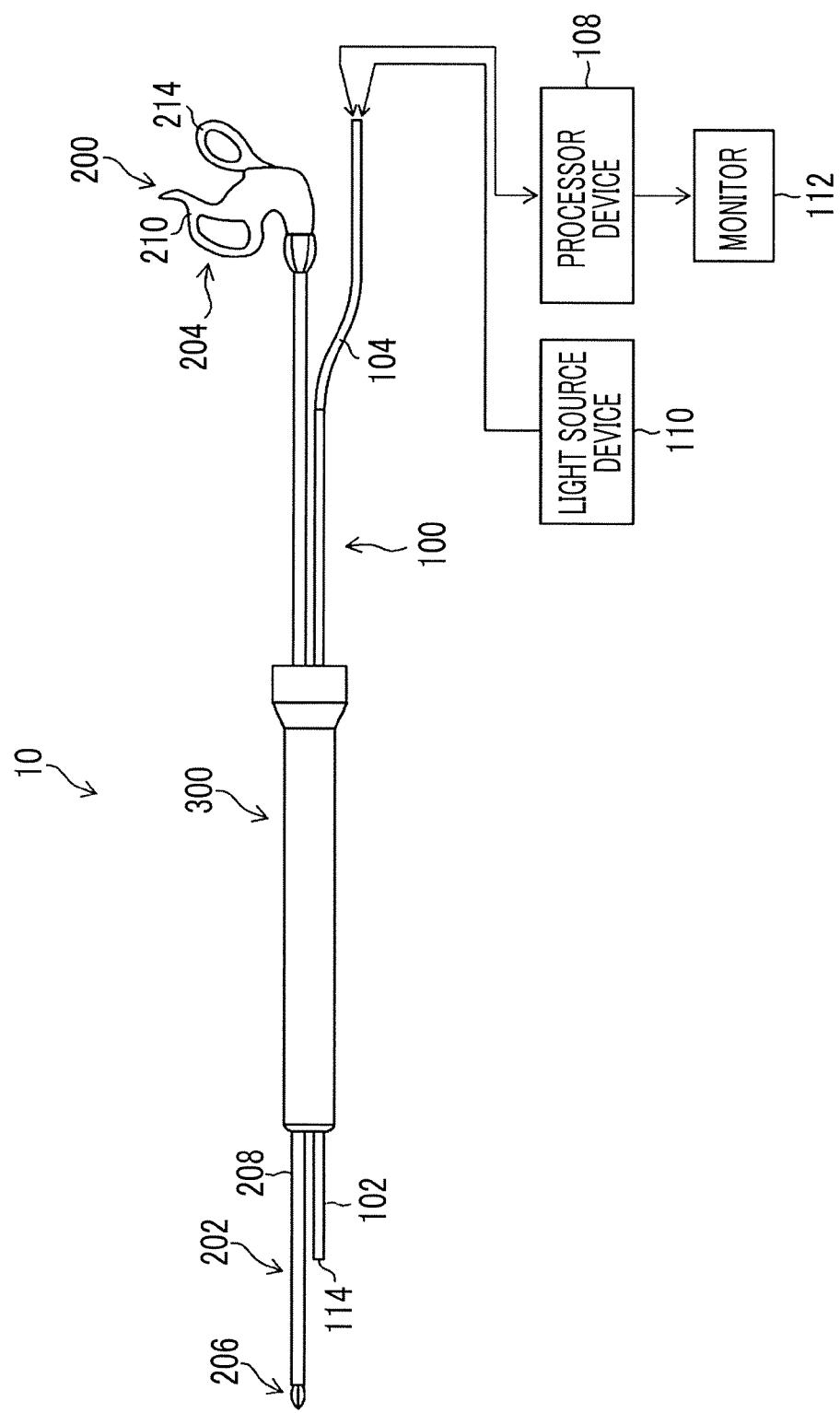
FIG. 1 is a schematic configuration view of an endoscopic surgical device related to one embodiment.

FIG. 1 is a schematic configuration view of an endoscopic surgical device related to the present embodiment. As illustrated in FIG. 1, an endoscopic surgical device 10 includes an endoscope 100 that observes the inside of a patient's body cavity as one form of a first medical instrument, a treatment tool 200 for examining or treating a diseased site within the patient's body cavity as one form of a second medical instrument, and an overtube 300 as a guide device that is inserted into a body wall and guides the endoscope 100 and the treatment tool 200 into the body cavity. In addition, the first medical instrument and the second medical instrument that is guided into the body cavity by the overtube 300 are not limited to specific types of medical instruments, and in a case where the first medical instrument having a first insertion part to be inserted into the body cavity and the second medical instrument having a second insertion part to be inserted into the body cavity are provided, arbitrary types of medical instruments can be adopted.

The endoscope 100 is, for example, a hard endoscope, such as a laparoscope, and includes an insertion part 102 (hereinafter referred to as "endoscope insertion part 102") that is inserted into a body cavity, and that has an outer peripheral part surrounded by an elongated hard tubular body, and a cable part 104 that is consecutively installed on a proximal end side of the endoscope insertion part 102 and that has an outer peripheral part surrounded by an elongated flexible tubular body.

The cable part 104 indicates a flexible cable portion in which a wire rod, such as a cable or a light guide, which extends from a proximal end of the endoscope insertion part 102, is housed by covering the wire rod with, for example, a flexible insulating member, such as polyvinyl chloride.

A connector (not illustrated) is provided at an end of the cable part 104 on its extension destination, and each of a processor device 108 that is a control device and a light source device 110 is detachably connected to the cable part via the connector. Additionally, the processor device 108 is connected to a monitor 112 via a cable.

Figure 2:
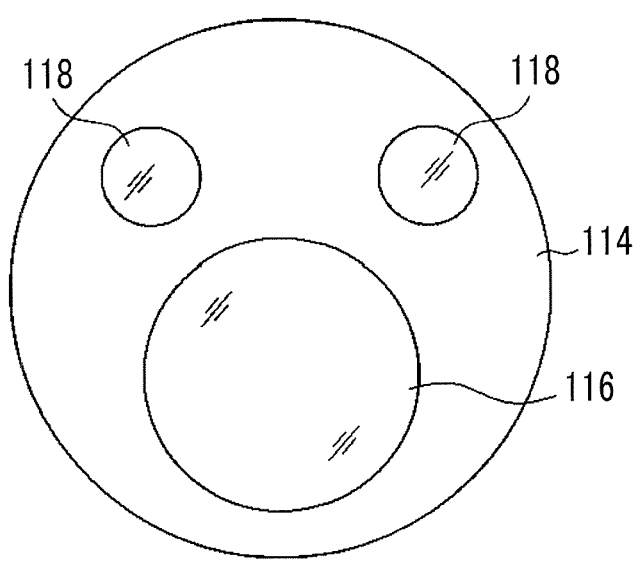
FIG. 2 is a plan view illustrating a distal end surface of an endoscope insertion part.

As illustrated in FIG. 2, a distal end surface 114 of the endoscope insertion part 102 is provided with an observation window 116 and illumination windows 118 and 118.

The observation window 116 is a constituent element of an observation part of the endoscope 100, and an objective lens of an observation optical system, and a solid image pickup element, such as a charge coupled device (CCD) image sensor or a complementary metal oxide semiconductor (CMOS) image sensor, which is disposed at an image pickup position of the objective lens, are disposed behind the observation window 116. A signal cable (not illustrated) connected to this solid image pickup element is inserted through the endoscope insertion part 102 and the cable part 104 of FIG. 1, is provided to extend up to the connector (not illustrated), and is connected to the processor device 108. An observation image picked up from the observation window 116 is formed on a light-receiving surface of the image pickup element, and is converted into electrical signals (image pickup signals), and the electrical signals are output to the processor device 108 via the signal cable and are converted into video signals. Then, the video signals are output to the monitor 112 connected to the processor device 108, and the observation image (endoscopic image) is displayed on a screen of the monitor 112.

An exit end of the light guide (not illustrated) is disposed behind the illumination windows 118 and 118 of FIG. 2. The light guide is inserted through the endoscope insertion part 102 and the cable part 104 of FIG. 1 and has an incident end disposed within the connector (not illustrated). Hence, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of illumination windows 118 is not limited, and the number thereof may be one or may be three or more.

As illustrated in FIG. 1, the treatment tool 200 consists of, for example, forceps, and includes an elongated insertion part 202 (hereinafter referred to as a "treatment tool insertion part (202)") that is inserted into a body cavity, an operating part 204 that is provided on the proximal end side of the treatment tool insertion part 202 and is gripped by a surgeon, and a treatment part 206 that is provided on a distal end side of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is coupled to the fixed handle 210 in a rotationally movable manner via a rotational movement pin. A proximal end part of the operating shaft is coupled to the movable handle 214.

The treatment part 206 is provided with a pair of gripping members that is openable and closable. The gripping members are coupled to a distal end part of the operating shaft via a driving mechanism (not illustrated). With the rotational movement operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, an ultrasonic device, and an aspirator.

As illustrated in FIG. 1, the overtube 300 allows the endoscope insertion part 102 and the treatment tool insertion part 202, which are inserted thereinto from the proximal end side, to be inserted therethrough and delivered from the distal end side. By inserting the overtube 300 into a body wall and having a proximal end side thereof disposed outside of the body and a distal end side thereof disposed within the body cavity, the endoscope insertion part 102 and the treatment tool insertion part 202 are guided into the body cavity with one overtube 300. Additionally, the overtube 300 includes an interlocking function of moving the endoscope insertion part 102 and the treatment tool insertion part 202 forward and backward in an interlocking manner as will be described below in detail. For example, the endoscope insertion part 102 can also be moved forward and backward by the forward and backward movement operation of only the treatment tool insertion part 202, and a suitable endoscopic image can be obtained without performing the forward and backward movement operation of the endoscope insertion part 102. The details of the configuration and working of the overtube 300 will be described below.

Figure 3:
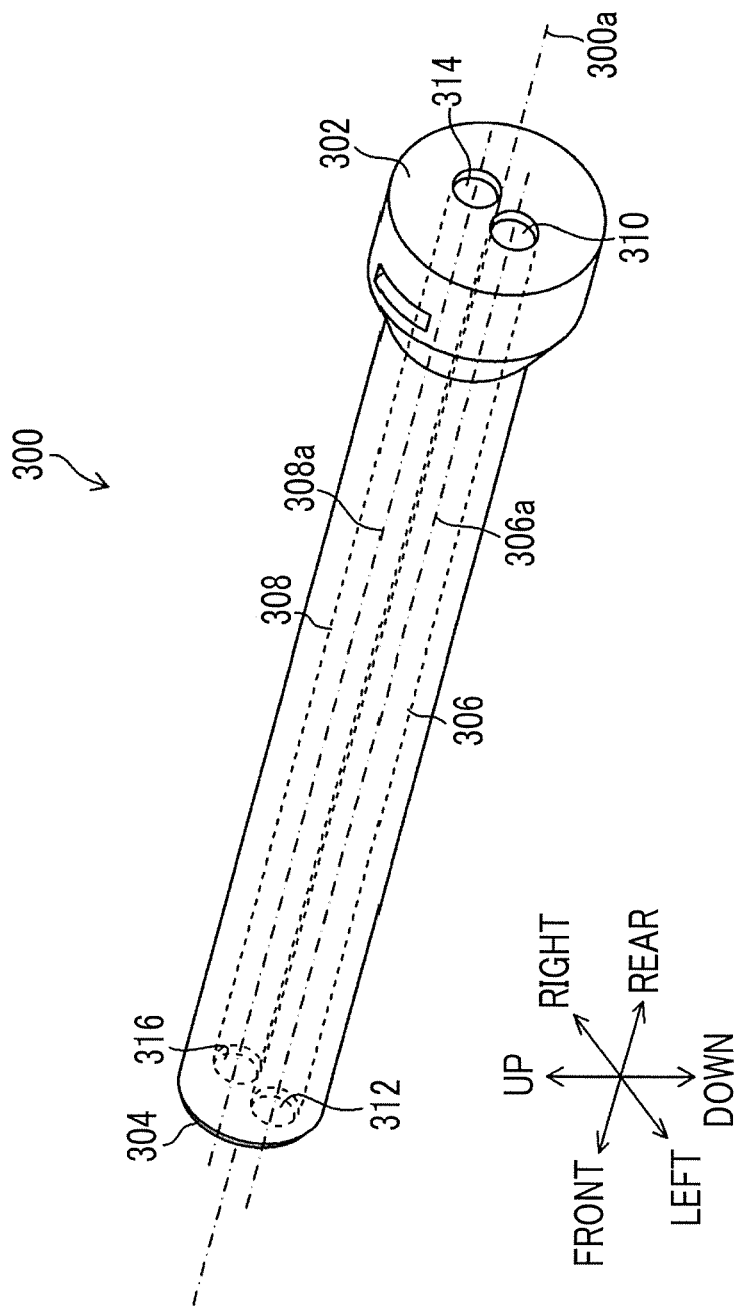
FIG. 3 is an external perspective view illustrating an overtube.

FIG. 3 is an external perspective view illustrating the overtube 300.

As illustrated in this drawing, the overtube 300 has an elongated cylindrical shape as a whole, and has an endoscope insertion passage 306 through which the endoscope insertion part 102 of the endoscope 100 is inserted so as to be movable forward and backward, and a treatment tool insertion passage 308 through which the treatment tool insertion part 202 of the treatment tool 200 is inserted so as to be movable forward and backward. These insertion passages are parallel to a reference axis 300a indicating a longitudinal axis that is a central axis of the overtube.

In a case where a central axis of the endoscope insertion passage 306 is referred to as an endoscope insertion axis 306a and a central axis of the treatment tool insertion passage 308 is referred to as a treatment tool insertion axis 308a, the endoscope insertion axis 306a and the treatment tool insertion axis 308a are parallel to each other, and is also parallel to the reference axis 300a. The endoscope insertion axis 306a and the treatment tool insertion axis 308a are equivalent to positions of the central axes of the endoscope insertion part 102 and the treatment tool insertion part 202 that are respectively inserted through the endoscope insertion passage 306 and the treatment tool insertion passage 308. Additionally, in the present embodiment, the reference axis 300a, the endoscope insertion axis 306a, and the treatment tool insertion axis 308a are disposed on the same plane. However, a configuration in which the reference axis 300a, the endoscope insertion axis 306a, and the treatment tool insertion axis 308a are disposed on the same plane may not be adopted.

In addition, regarding the position and orientation of a space where the overtube 300 has been disposed, terms called front, rear, left, right, up, and down are used with the orientation from the proximal end surface 302 in a direction along the reference axis 300a to the distal end surface 304 defined as the forward and with the orientation from the reference axis 300a to the endoscope insertion axis 306a defined as the left.

The proximal end surface 302 of the overtube 300 is provided with a first proximal end opening 310 that is a proximal end opening that allows the endoscope insertion part 102 to be inserted into the endoscope insertion passage 306 therethrough, and a second proximal end opening 314 that is proximal end opening that allows the treatment tool insertion part 202 to be inserted into the treatment tool insertion passage 308 therethrough.

The distal end surface 304 of the overtube 300 is provided with a first distal end opening 312 that is a distal end opening that allows the endoscope insertion part 102 to be inserted into the endoscope insertion passage 306 to be and delivered to the outside therethrough, and a second distal end opening 316 that is a distal end opening that allows the treatment tool insertion part 202 to be inserted into the treatment tool insertion passage 308 to be and delivered to the outside therethrough.

Here, before describing the embodiment of the invention with respect to the internal structure of the overtube 300, a reference form serving as a reference for the configuration and working effects of the invention will be described with reference to FIGS. 4 to 13. The embodiment of the invention will be described below with reference to FIGS. 14 to 25.

Figure 4:
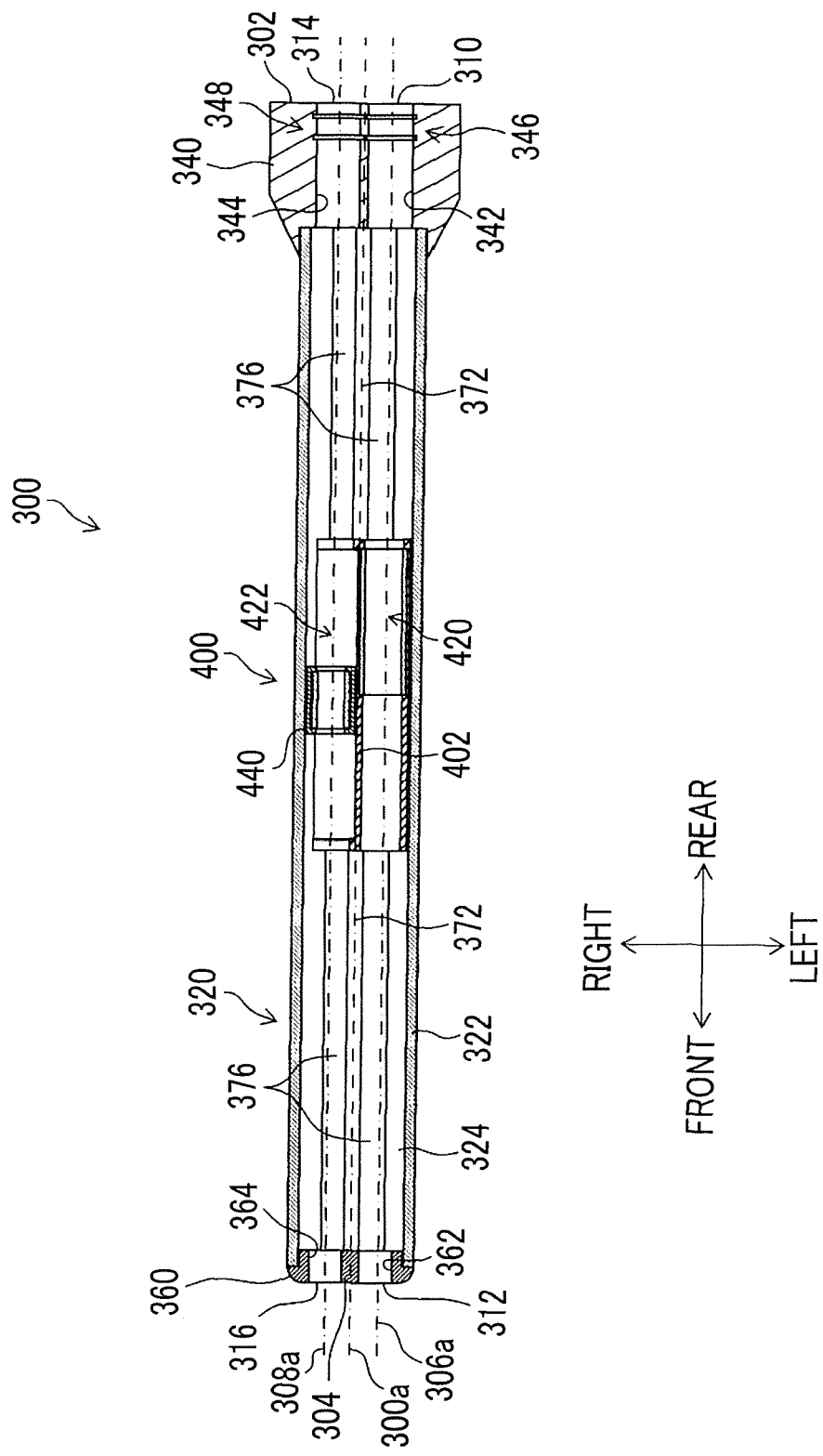
FIG. 4 is a cross-sectional view illustrating a reference form that is a reference for the embodiment of the invention with respect to the internal structure of the overtube.

FIG. 4 is a cross-sectional view illustrating a reference form of the internal structure of the overtube 300, and illustrates a cross section cut in a plane that includes the reference axis 300a and is orthogonal to an upward-downward direction (cut in a leftward-rightward direction along the reference axis 300a).

As illustrated in this drawing, the overtube 300 has a long tubular overtube body 320 that occupies substantially the entire area in the forward-backward direction, a proximal end cap 340 that is attached to a rear end (proximal end) of the overtube 300, a distal end cap 360 that is attached to a distal end part, and a slider 400 that is one form of the interlocking member disposed inside the overtube 300.

The long tubular overtube body 320 is formed in an elongated cylindrical shape having the reference axis 300a as a central axis using hard resins, metals, or the like, and has an outer wall 322 that surrounds an outer periphery, and a cavity part 324 that penetrates from a proximal end of the long tubular overtube body 320 to a distal end thereof.

The cavity part 324 includes spaces serving as the endoscope insertion passage 306 and the treatment tool insertion passage 308, and houses the slider 400 and the like.

The proximal end cap 340 is formed in a columnar shape of which the diameter is made larger than the external diameter of the long tubular overtube body 320 using hard resins, metals, or the like, and a rear end surface thereof constitutes the proximal end surface 302 of the overtube 300. The proximal end cap 340 is provided with a through-hole 342 and a through-hole 344 that form a portion of the endoscope insertion passage 306 and a portion of the treatment tool insertion passage 308, respectively. In the proximal end surface 302, an opening of the through-hole 342 is equivalent to the above-described first proximal end opening 310, and an opening of the through-hole 344 is equivalent to the above-described second proximal end opening 314.

Additionally, the through-holes 342 and 344 are respectively provided with valve members 346 and 348. The valve members 346 and 348, for example, open in a case where the endoscope insertion part 102 and the treatment tool insertion part 202 are inserted therethrough and come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of a pneumoperitoneum gas injected into the body cavity to the outside of the body.

The distal end cap 360 is formed of hard resins, metals, or the like, and a front end surface thereof constitutes the distal end surface 304 of the overtube 300. The distal end cap 360 is provided with a through-hole 362 and a through-hole 364 that form a portion of the endoscope insertion passage 306 and a portion of the treatment tool insertion passage 308, respectively. In the distal end surface 304, an opening of the through-hole 362 is equivalent to the above-described first distal end opening 312, and an opening of the through-hole 364 is equivalent to the second distal end opening 316.

In addition, the long tubular overtube body 320, the proximal end cap 340, and the distal end cap 360 show one form of constituent members that constitutes the overtube 300, and the overtube 300 is not limited to the configuration of the present embodiment. For example, the long tubular overtube body 320 and the proximal end cap 340 or the long tubular overtube body 320 and the distal end cap 360 may be integrally formed, or may be integrally formed in their entirety.

Additionally, the overtube 300 may be a tubular member through which the first insertion part of the first medical instrument and the second insertion part of the second medical instrument are inserted and which guides the first insertion part and the second insertion part into the body cavity.

The slider 400 is housed within (the cavity part 324) the long tubular overtube body 320, and is supported so as to be movable forward and backward in the direction of the reference axis 300a. The slider 400 shows an embodiment of the interlocking member that is coupled to the endoscope insertion part 102 inserted through the endoscope insertion passage 306 and the treatment tool insertion part 202 inserted through the treatment tool insertion passage 308, and interlocks the endoscope insertion part 102 and the treatment tool insertion part 202 with each other to move these insertion parts forward and backward in the forward-backward direction (axial direction).

Particularly, the slider 400 is an interlocking member that has a non-sensing region where the forward and backward movement of either the endoscope insertion part 102 or the treatment tool insertion part 202 in the forward-backward direction (axial direction) does not interlock with the movement of the other, that is, moves independently and a sensing region where the forward and backward movement of either the endoscope insertion part 102 or the treatment tool insertion part 202 interlocks with the movement of the other, and that changes the relative position of a distal end of the endoscope 100 with respect to a distal end of the treatment tool 200 in the direction of the reference axis 300a of the overtube 300 in the non-sensing region. That is, the endoscope insertion part 102 is adapted to interlock with the forward and backward movement of the treatment tool insertion part 202 in the axial direction with play by the slider 400.

Figure 5:
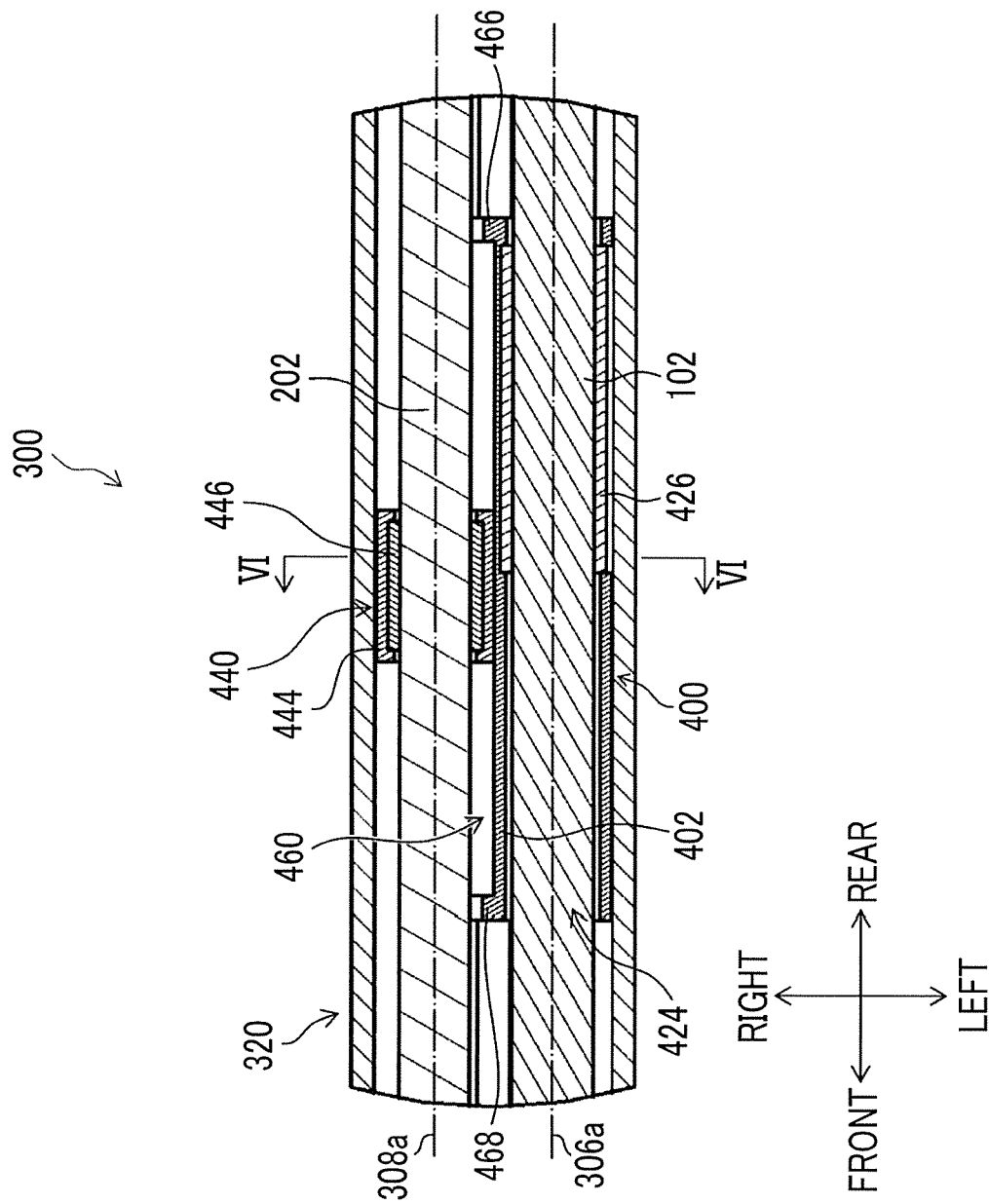
FIG. 5 is an enlarged cross-sectional view illustrating a portion of FIG. 4 in an enlarged manner.
Figure 6:
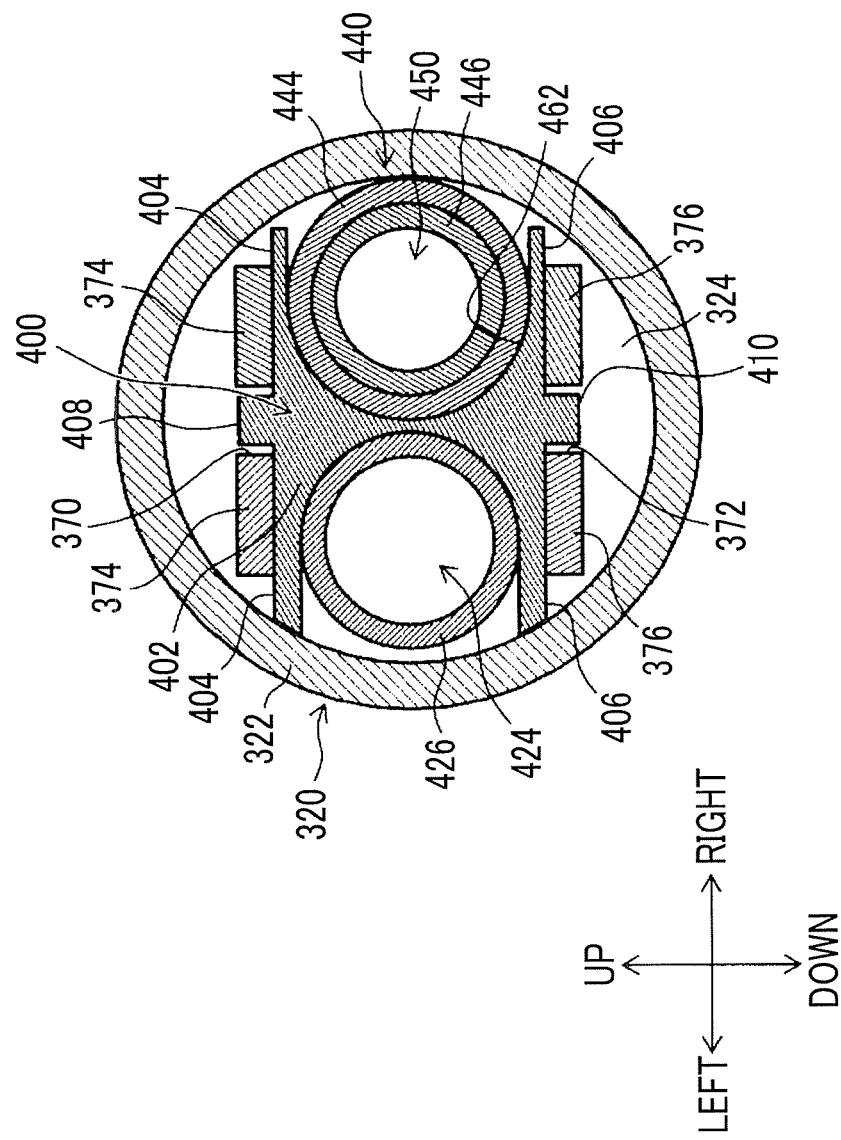
FIG. 6 is a cross-sectional view when viewed from arrow VI-VI in FIG. 5.

FIG. 5 is an enlarged cross-sectional view illustrating a portion, in which the slider 400 is disposed in FIG. 4, in an enlarged manner, and illustrates a state where the endoscope insertion part 102 and the treatment tool insertion part 202 have been inserted through the endoscope insertion passage 306 and the treatment tool insertion passage 308, respectively. FIG. 6 is a cross-sectional view when viewed from arrow VI-VI in FIG. 5.

Figure 7:
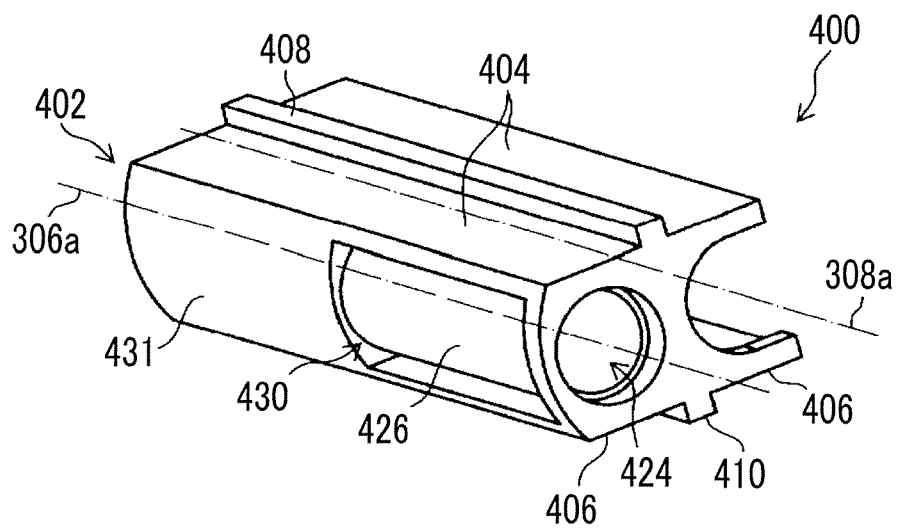
FIG. 7 is a perspective view illustrating a slider (interlocking member) in the reference form of FIG. 4 from the rear upper left side.
Figure 8:
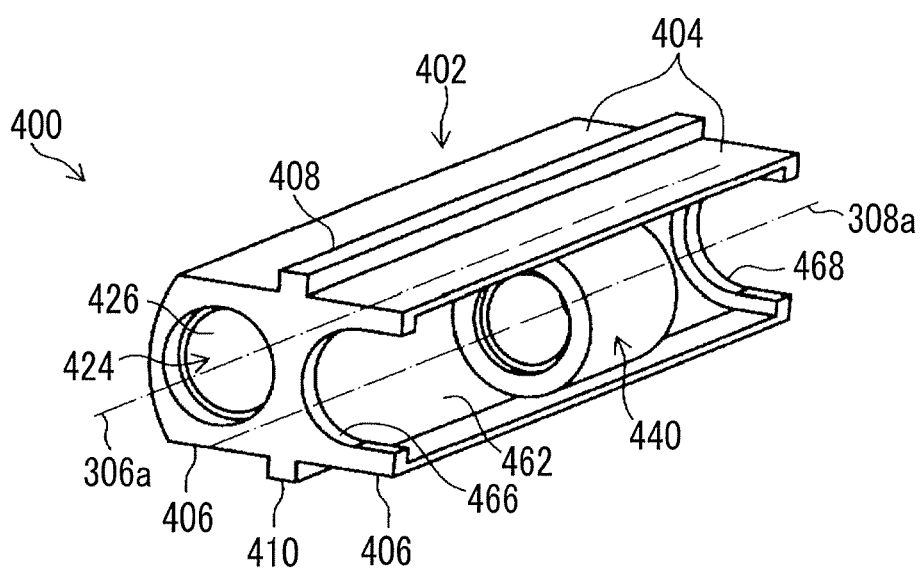
FIG. 8 is a perspective view illustrating the slider (interlocking member) in the reference form of FIG. 4 from the rear upper right side.

Additionally, FIGS. 7 and 8 are respectively perspective views illustrating the slider 400 from the rear upper left and from the rear upper right.

As illustrated in these drawings, the slider 400 has a slider body 402 that holds components of the slider 400. As illustrated in FIG. 6, protruding strips 408 and 410 that extend in the direction (forward-backward direction) of the reference axis 300a are formed on a flat upper surface 404 (refer to FIGS. 7 and 8) and a flat lower surface 406 of the slider body 402.

Meanwhile, a pair of left and right long plate-shaped guide plates 376 and 374 and a pair of left and right long plate-shaped guide plates 376 and 376, which are laid between the proximal end cap 340 and the distal end cap 360 and illustrated in FIG. 6, are respectively supported by an upper part and a lower part within the long tubular overtube body 320, and guide grooves 370 and 372, which extend in the direction of the reference axis 300a from the proximal end cap 340 to the distal end cap 360, are formed by a gap between the guide plates 374 and 374 and a gap between the guide plates 374 and 376.

The protruding strips 408 and 410 of the slider body 402 are respectively fitted into the guide grooves 370 and 372 within the long tubular overtube body 320, and the upper surface 404 and the lower surface 406 are disposed in a state where these surfaces have contacted or approached the guide plates 374 and 374 and the guide plates 376 and 376.

Accordingly, the slider 400 is supported so as to be movable forward and backward in the forward-backward direction within the long tubular overtube body 320, and is supported in a state where the movement of the slider in the upward-downward direction and in the leftward-rightward direction and the rotation of the slider in all directions (direction around three axes including a forward-backward axis, a leftward-rightward axis, and an upward-downward direction) are restricted (a state where the rotation of the slider around at least the reference axis 300a is impossible). Additionally, the slider 400 moves forward and backward within a movable range having a position where the slider abuts against the proximal end cap 340 as a rear end, and having a position where the slider abuts against the distal end cap 360 as a front end.

In addition, the guide grooves 370 and 372 may not be formed by the guide plates 374 and 374 and the guide plates 376 and 376 disposed within the long tubular overtube body 320, and may be formed in the outer wall 322 of the long tubular overtube body 320 or may be formed by other configurations.

Additionally, the slider 400, as illustrated in FIG. 4, has a left endoscope coupling part 420 that is coupled to (engaged with) the endoscope insertion part 102, and a right treatment tool coupling part 422 that is coupled to (engaged with) the treatment tool insertion part 202.

The endoscope coupling part 420 provided on the left side of the slider body 402 secures a space serving as the endoscope insertion passage 306, within the long tubular overtube body 320, and as illustrated in FIG. 5, includes a through-hole 424 (refer to FIGS. 6, 7, and 8) into which the endoscope insertion part 102 is inserted, and a pressure-contact member 426 that is fixed to the through-hole 424 and is brought into pressure contact with the outer peripheral surface (side surface) of the endoscope insertion part 102 inserted through the endoscope insertion passage 306.

The pressure-contact member 426 is formed in a cylindrical shape using elastic materials, such as elastic rubber, as illustrated in FIGS. 6 and 7, and is fitted into the through-hole 424 of the slider body 402 up to a position coaxial with the through-hole 424 from an opening 430 formed on a left side surface 431 of the slider body 402 and fixed to the slider body 402, as illustrated in FIG. 7.

Accordingly, when the endoscope insertion part 102 has been inserted through the endoscope insertion passage 306, as illustrated in FIG. 5, the endoscope insertion part 102 is inserted through the through-hole 424, and the pressure-contact member 426 is brought into pressure contact with (engaged with) the outer peripheral surface of the endoscope insertion part 102, and the central axis of the endoscope insertion part 102 is disposed coaxially with the endoscope insertion axis 306a.

The endoscope insertion part 102 and the slider 400 (slider body 402) are coupled to (engaged with) each other in an interlocking manner via the pressure-contact member 426, and the slider 400 (slider body 402) also integrally moves forward and backward in an interlocking manner with the forward and backward movement of the endoscope insertion part 102 in the forward-backward direction (axial direction).

In addition, since the coupling herein is based on the elastic force of the pressure-contact member 426, the engagement position (the position of the endoscope insertion part 102 where the slider 400 is engaged) of the endoscope insertion part 102 coupled to the slider 400 (slider body 402) can be arbitrarily adjusted.

The treatment tool coupling part 422 provided on the right side of the slider body 402 as illustrated in FIG. 4, as illustrated in FIG. 8, includes a sleeve 440 (refer to FIGS. 6 and 8) that is coupled to the treatment tool insertion part 202, and a guide part 460 that guides the sleeve 440 so as to be movable forward and backward in the forward-backward direction.

The sleeve 440, as illustrated in FIG. 6, includes a sleeve body 444 (frame body) formed in a cylindrical shape, and a pressure-contact member 446 fixed to the inside of the sleeve body 444. The pressure-contact member 446 is formed in a cylindrical shape using elastic materials, such as elastic rubber.

Accordingly, when the treatment tool insertion part 202 has been inserted through the treatment tool insertion passage 308, as illustrated in FIG. 5, the treatment tool insertion part 202 is inserted through the inside (the through-hole 450 of FIG. 6) of the pressure-contact member 446, the pressure-contact member 446 is brought into pressure contact with (engaged with) the outer peripheral surface of the treatment tool insertion part 202, and the central axis of the treatment tool insertion part 202 is disposed coaxially with the treatment tool insertion axis 308a.

The treatment tool insertion part 202 and the sleeve 440 are coupled with each other in an interlocking manner via the pressure-contact member 446, and the sleeve 440 also integrally moves forward and backward in an interlocking manner with the forward and backward movement of the treatment tool insertion part 202 in the forward-backward direction (axial direction).

Additionally, the sleeve 440 also rotates with respect to the slider body 402 in an interlocking manner with the rotation of the treatment tool insertion part 202 around its axis.

In addition, since the coupling between the treatment tool insertion part 202 and the sleeve 440 herein is based on the elastic force of the pressure-contact member 446, the engagement position (the position of the treatment tool insertion part 202 where the sleeve 440 is engaged) of the treatment tool insertion part 202 coupled to the sleeve 440 can be arbitrarily adjusted.

Meanwhile, the guide part 460 of the treatment tool coupling part 422, as illustrated in FIGS. 6 and 8, is formed by a space surrounded by a guide surface 462 of the slider body 402 that extends in the direction of the reference axis 300a (treatment tool insertion axis 308a), within the cavity part 324 of the long tubular overtube body 320, and an inner peripheral surface of the long tubular overtube body 320. The sleeve 440 is housed and disposed in the space of the guide part 460, is supported so as to be movable in the forward-backward direction and rotatable around its axis, and is supported in a state where the movement of the sleeve in the upward-downward direction and in the leftward-rightward direction is restricted.

Additionally, the guide part 460 is provided so as to fall within a range from a proximal end of the slider body 402 to a distal end thereof, and as illustrated in FIGS. 5 and 8, has end edge parts 466 and 468, which are formed to protrude in a direction orthogonal to the guide surface 462 along an end edge of the guide surface 462, respectively, on the proximal end side and the distal end side of the slider body 402.

The end edge parts 466 and 468 abut against the end of the sleeve 440 to restrict the movement of the sleeve 440, when the sleeve 440 disposed in the space of the guide part 460 moves forward and backward in the forward-backward direction.

Hence, the sleeve 440 moves forward and backward within a movable range having a position where the sleeve abuts against the end edge part 466 as a rear end, and having a position where the sleeve abuts against the end edge part 468 as a front end.

The working of the slider 400 configured as described above will be described together with the operation when the treatment of a diseased site within a patient's body cavity is performed using the endoscopic surgical device 10.

Figure 12:
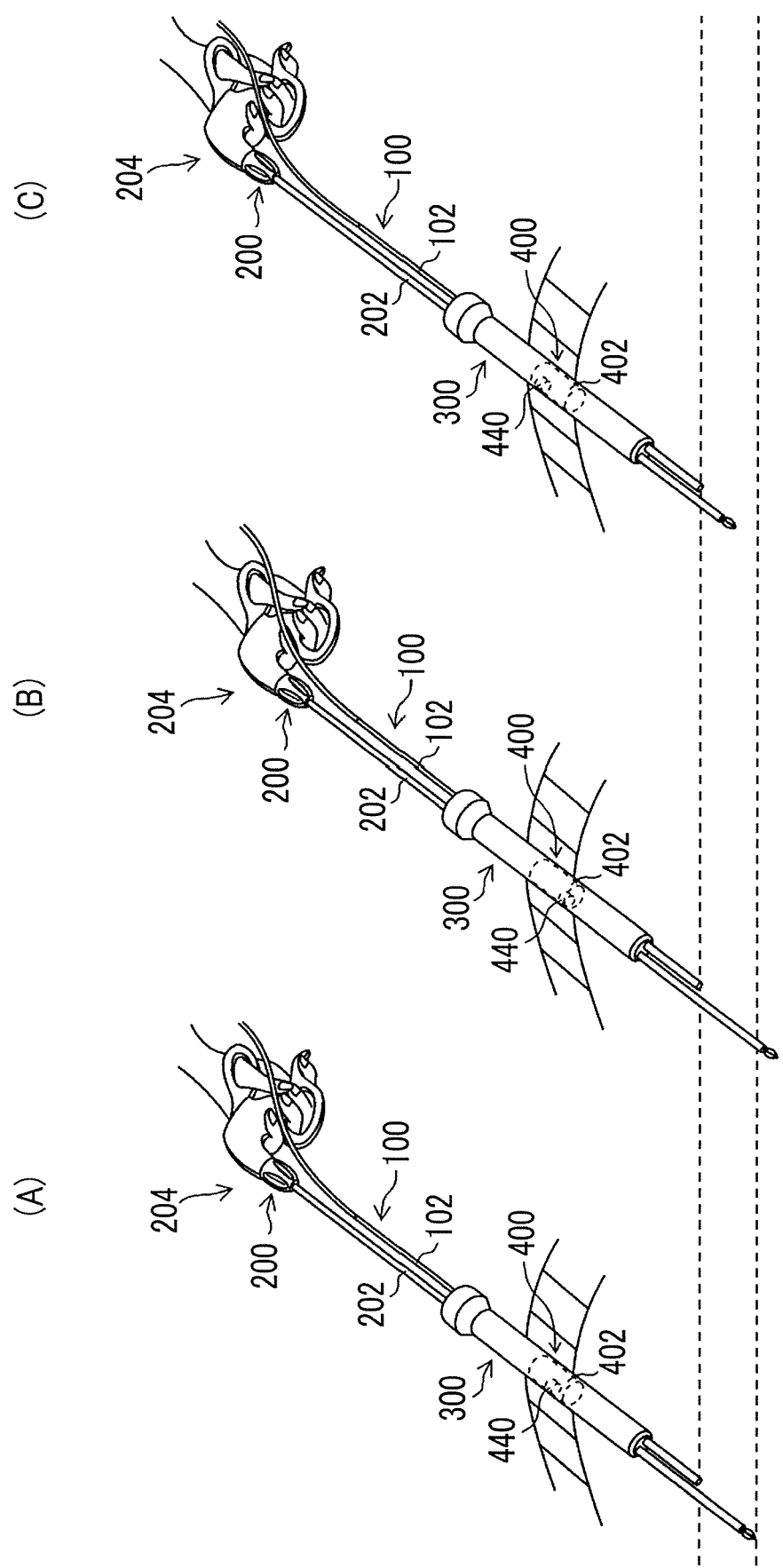
FIG. 12 is an explanatory view illustrating the aspect of the operation when performing treatment of a diseased site within a patient's body cavity using the endoscopic surgical device, portion (A) illustrates a pre-operation state, portion (B) illustrates a state where a treatment tool insertion part is operated forward in a non-sensing region, and portion (C) illustrates a state where the treatment tool insertion part is operated backward in the non-sensing region.

First, as illustrated in portion (A) of FIG. 12, after the overtube 300 is inserted into a patient's body wall and a pneumoperitoneum gas is injected into a body cavity, the endoscope 100 (endoscope insertion part 102) and the treatment tool 200 (treatment tool insertion part 202) are respectively inserted into the endoscope insertion passage 306 and the treatment tool insertion passage 308 of the overtube 300, and the endoscope insertion part 102 and the treatment tool insertion part 202 are mounted on the overtube 300. In this case, the endoscope insertion part 102 is coupled to the slider body 402 of the slider 400, and the treatment tool insertion part 202 is coupled to the sleeve 440 of the slider 400.

Figure 9:
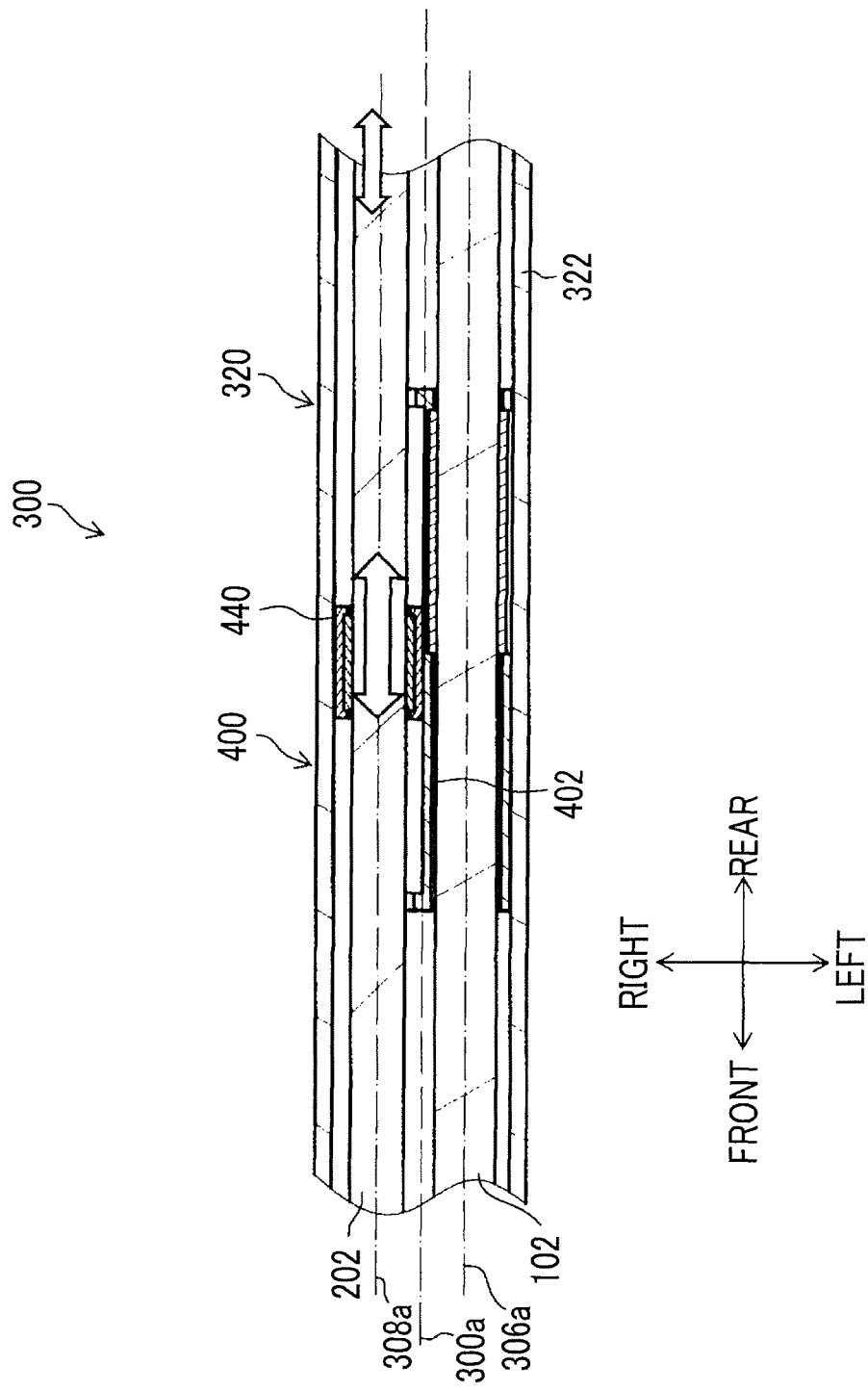
FIG. 9 is an explanatory view used for the description of the working of the slider (interlocking member) in the reference form of FIG. 4.

Supposing the state of portion (A) of FIG. 12 is a state where the sleeve 440 reaches neither the front end nor the rear end of the movable range thereof with respect to of the slider body 402 (guide part 460) as illustrated in FIG. 9, in a case where a surgeon minutely moves the treatment tool insertion part 202 forward with his/her hand that is gripping the operating part 204 of the treatment tool 200, the slider body 402 does not move with respect to the overtube 300 (long tubular overtube body 320), but the sleeve 440 moves forward with respect to the slider body 402 within the movable range thereof with respect to the slider body 402. For that reason, with respect to the forward movement of the treatment tool insertion part 202 until the sleeve 440 reaches the front end of the movable range thereof with respect to the slider body 402, as illustrated in portion (B) of FIG. 12, only the treatment tool insertion part 202 moves forward in a state where the endoscope insertion part 102 is stationary. That is, the slider 400 has the non-sensing region where the endoscope insertion part 102 does not interlock with the forward and backward movement of the treatment tool insertion part 202, and the forward movement operation of the treatment tool 200 at this time becomes a forward and backward movement operation of the slider 400 in the non-sensing region.

Similarly, supposing the state of portion (A) of FIG. 12 is a state where the sleeve 440 reaches neither the front end nor the rear end of the movable range thereof with respect to of the slider body 402 (guide part 460) as illustrated FIG. 9, in a case where the surgeon minutely moves the treatment tool insertion part 202 backward with his/her hand that is gripping the operating part 204 of the treatment tool 200, the slider body 402 does not move with respect to the overtube 300 (long tubular overtube body 320), but the sleeve 440 moves backward with respect to the slider body 402 within the movable range thereof with respect to the slider body 402. For that reason, with respect to the backward movement of the treatment tool insertion part 202 until the sleeve 440 reaches the rear end of the movable range thereof with respect to the slider body 402, as illustrated in portion (C) of FIG. 12, only the treatment tool insertion part 202 moves backward in a state where the endoscope insertion part 102 is stationary. That is, the backward movement operation of the treatment tool 200 at this time becomes a backward movement operation of the slider 400 in the non-sensing region.

Hence, since the endoscope 100 does not move forward and backward with respect to the minute forward and backward movement operation of the treatment tool 200, that is, the forward and backward movement operation thereof in the non-sensing region, the range of an observation site, such as a distal end site of the treatment tool 200 or a body cavity inner site, to be displayed on the monitor 112 as an endoscopic image does not change, and the size of an image of the observation site can be prevented from fluctuating according to minute displacement of the treatment tool 200. Accordingly, a sense of perspective can be suitably maintained, and a stable endoscopic image can be provided.

Figure 10:
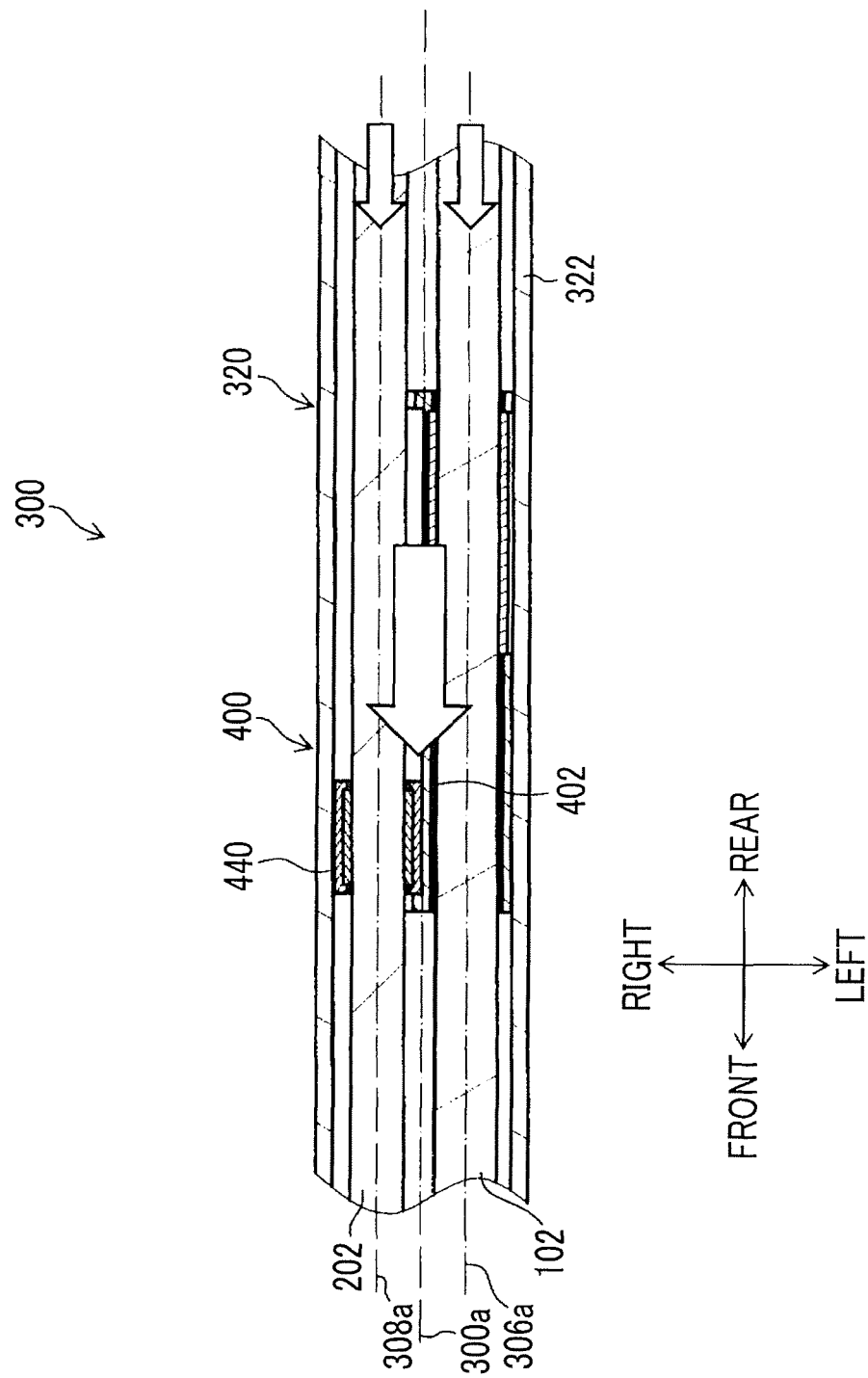
FIG. 10 is an explanatory view used for the description of the working of the slider (interlocking member) in the reference form of FIG. 4.

Meanwhile, in a case where the surgeon largely moves the treatment tool insertion part 202 forward with his/her hand that is gripping the operating part 204 of the treatment tool 200 in a state where the sleeve 440 reaches neither the front end nor the rear end of the movable range thereof with respect the slider body 402 as illustrated in FIG. 9, a state where the sleeve 440 reaches the front end of the movable range thereof with respect to the slider body 402 as illustrated in FIG. 10 is brought into after the forward movement of the sleeve 440 of the slider 400 in the non-sensing region until it abuts against the front end of the movable range.

Then, in a case where the treatment tool insertion part 202 further moves forward, the sleeve 440 and the slider body 402 moves forward with respect to the long tubular overtube body 320 together with the treatment tool insertion part 202, and the endoscope insertion part 102 moves forward in an interlocking manner with the treatment tool insertion part 202.

Figure 13:
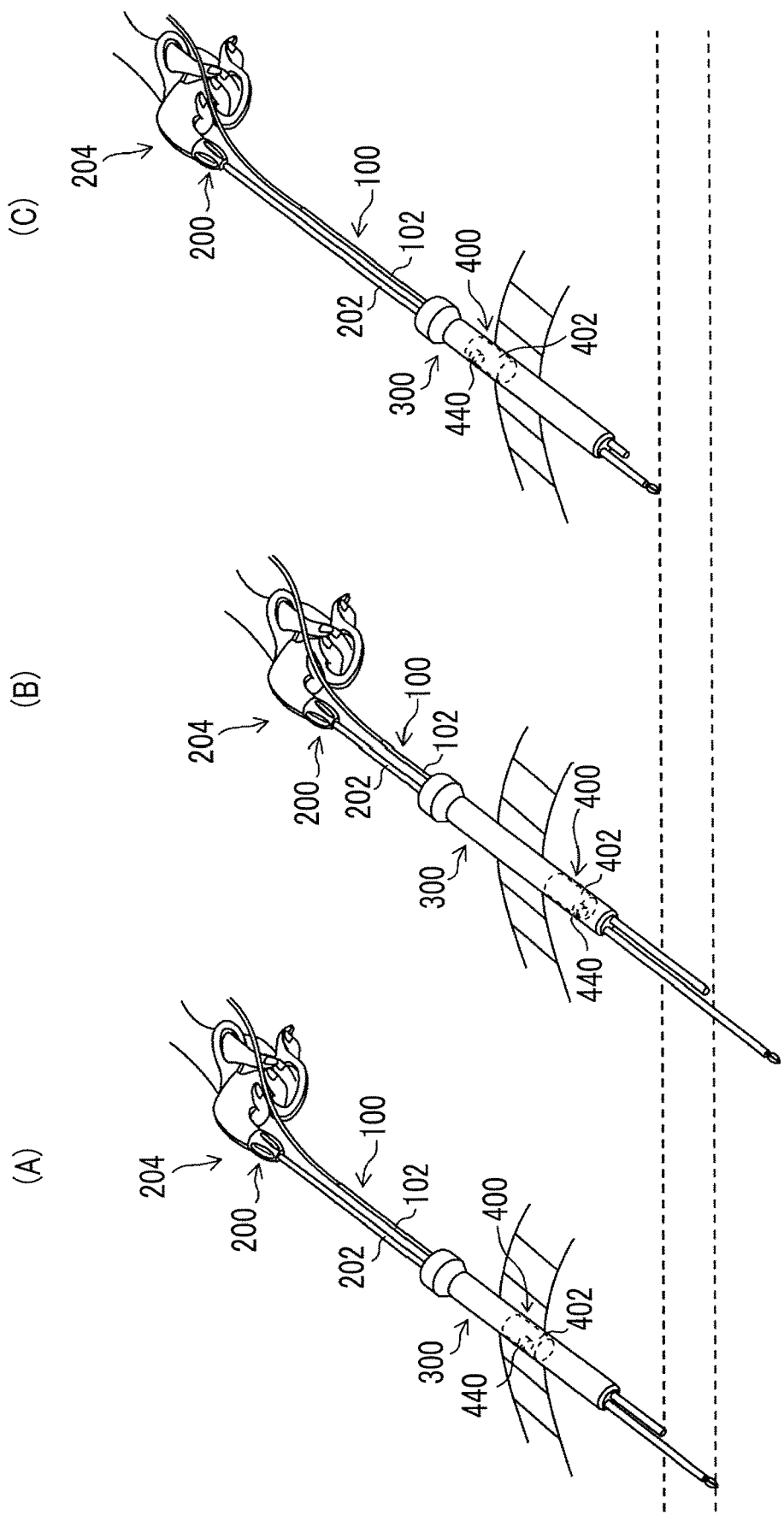
FIG. 13 is an explanatory view illustrating the aspect of the operation when performing treatment of a diseased site within a patient's body cavity using the endoscopic surgical device, portion (A) illustrates a pre-operation state, portion (B) illustrates a state where a treatment tool insertion part is operated forward in a sensing region, and portion (C) illustrates a state where the treatment tool insertion part is operated backward in the sensing region.

For that reason, with respect to the forward movement of the treatment tool insertion part 202 after the sleeve 440 reaches the front end of the movable range thereof with respect to the slider body 402, the treatment tool insertion part 202 moves forward in an interlocking manner with the endoscope insertion part 102 as illustrated in portion (B) of FIG. 13, compared to the state of portion (A) of FIG. 13 illustrating the same state as portion (A) of FIG. 12. That is, the slider 400 has the sensing region where the endoscope insertion part 102 interlocks with the forward and backward movement of the treatment tool insertion part 202, and the forward movement operation of the treatment tool 200 at this time becomes a forward movement operation of the slider 400 in the sensing region.

Figure 11:
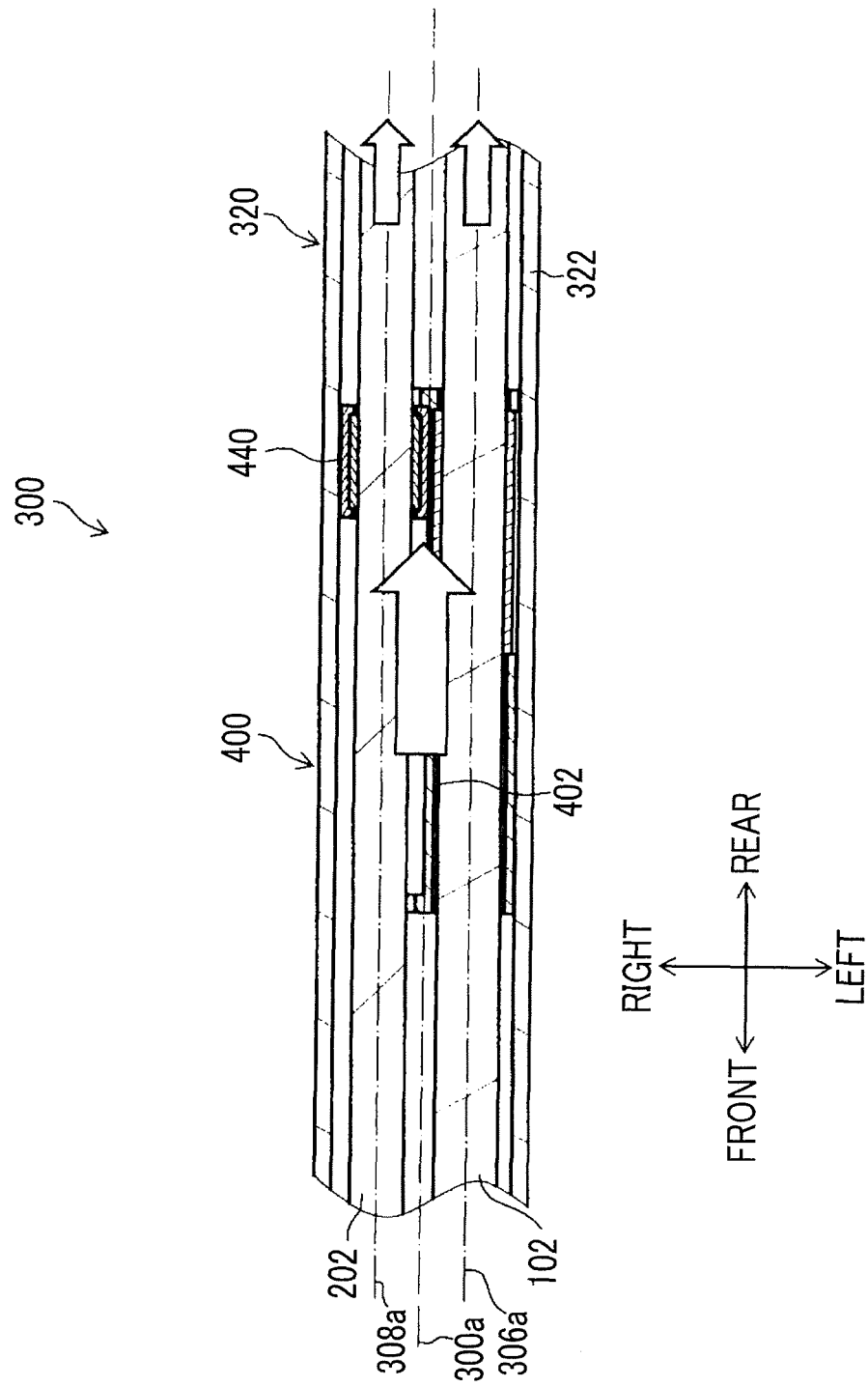
FIG. 11 is an explanatory view used for the description of the working of the slider (interlocking member) in the reference form of FIG. 4.

Similarly, in a case where the surgeon largely moves the treatment tool insertion part 202 backward with his/her hand that is gripping the operating part 204 of the treatment tool 200 in a state where the sleeve 440 reaches neither the front end nor the rear end of the movable range thereof with respect the slider body 402 as illustrated in FIG. 9, a state where the sleeve 440 reaches the rear end of the movable range thereof with respect to the slider body 402 as illustrated in FIG. 11 is brought into after the backward movement of the sleeve 440 of the slider 400 in the non-sensing region until it abuts against the rear end of the movable range.

Then, in a case where the treatment tool insertion part 202 further moves backward, the sleeve 440 and the slider body 402 moves backward with respect to the long tubular overtube body 320 together with the treatment tool insertion part 202, and the endoscope insertion part 102 moves backward in an interlocking manner with the treatment tool insertion part 202.

For that reason, with respect to the backward movement of the treatment tool insertion part 202 after the sleeve 440 reaches the rear end of the movable range thereof with respect to the slider body 402, as illustrated in portion (C) of FIG. 13, the endoscope insertion part 102 moves backward in an interlocking manner with the treatment tool insertion part 202. That is, the backward movement operation of the treatment tool 200 at this time becomes a backward movement operation of the slider 400 in the sensing region.

Hence, since the endoscope 100 moves forward and backward with respect to a large forward and backward movement operation of the treatment tool 200, that is, the forward and backward movement operation thereof in the sensing region, the range of an observation site that appears in an endoscopic image to be displayed on the monitor 112 is continuously changed so as to follow the forward and backward movement of the treatment tool 200.

Since the size of images of observation sites other than the distal end site of the treatment tool 200 that appears in the endoscopic image according to the operation of the treatment tool 200, and the size of the range of the observation site changes, the surgeon can simply obtain a desired image.

As described above, in a case where the displacement of the treatment tool insertion part 202 in the axial direction is large (in a case where a large amplitude of forward and backward movement operation has been performed) when a surgeon has moved the treatment tool insertion part 202 forward and backward in the axial direction, the endoscope insertion part 102 also moves forward and backward in an interlocking manner in the forward-backward direction, in the upward-downward direction, and in the rightward-leftward direction. Thus, the visual field, orientation, and the like of the endoscope 100 can be changed as intended by a surgeon.

Additionally, the visual field is always given to pick up an image of the distal end site of the treatment tool 200 and consequently, an image that is optimal for treatment is automatically provided. In a case where it is desired to check sites other than a site to be treated, the checking can be performed by moving the treatment tool insertion part 202, and a surgeon can perform operations as desired.

Hence, an assistant (endoscopic technician) who operates the endoscope 100 apart from the surgeon can be made unnecessary, and a troublesome condition in which the surgeon should instruct an assistant about the visual field, orientation, and the like of the endoscope 100 serially can be eliminated.

Additionally, in a case where the displacement of the treatment tool insertion part 202 in the axial direction is small (in a case where a small amplitude of forward and backward movement operation has been performed), the endoscope insertion part 102 does not interlock. Therefore, an endoscopic image can be prevented from fluctuating unnecessarily, a sense of perspective can be suitably maintained, and a stable endoscopic image can be provided.

Next, the internal structure of the overtube 300 of the embodiment of the invention will be described. Although the above reference form adopts the slider 400 as the interlocking member that interlocks the endoscope insertion part 102 and the treatment tool insertion part 202, an interlocking member that is an interlocking member having a simple configuration with respect to the slider 400 and exhibits the same effects as those of the slider 400 is adopted in the embodiment of the invention.

Figure 14:
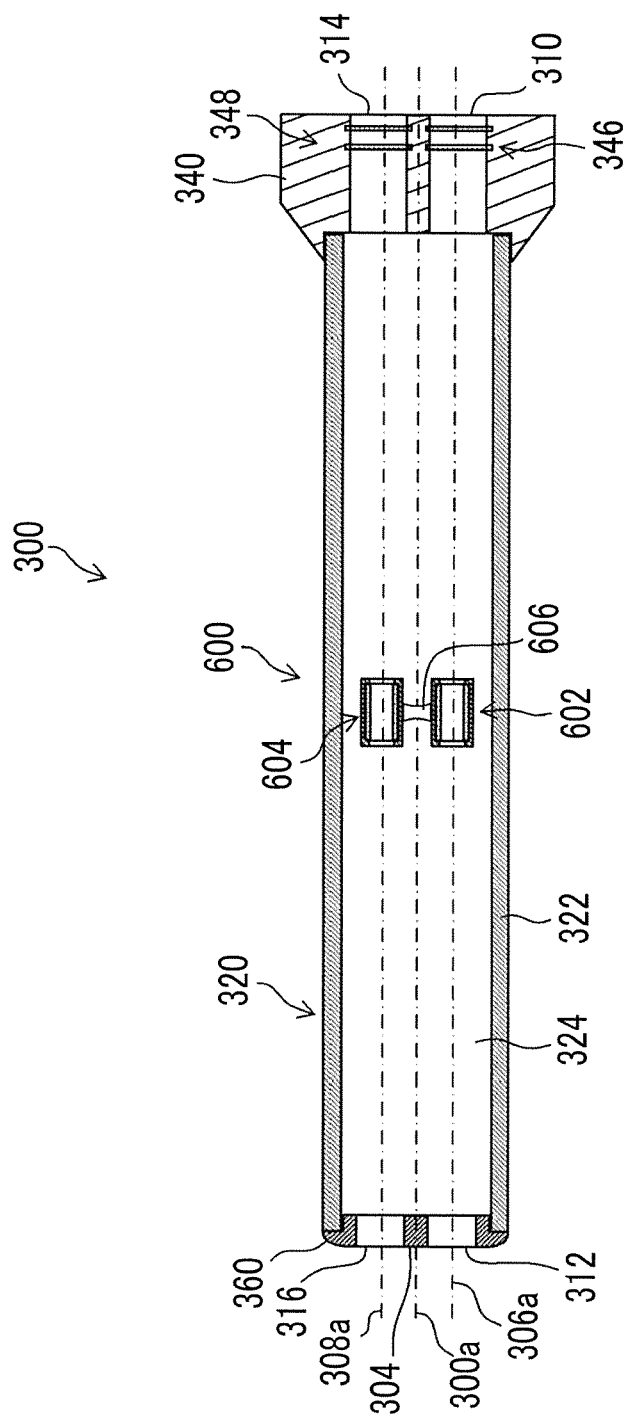
FIG. 14 is a cross-sectional view illustrating the configuration of an interlocking member of the embodiment of the invention in a cross section of the overtube cut along a reference axis.
Figure 15:
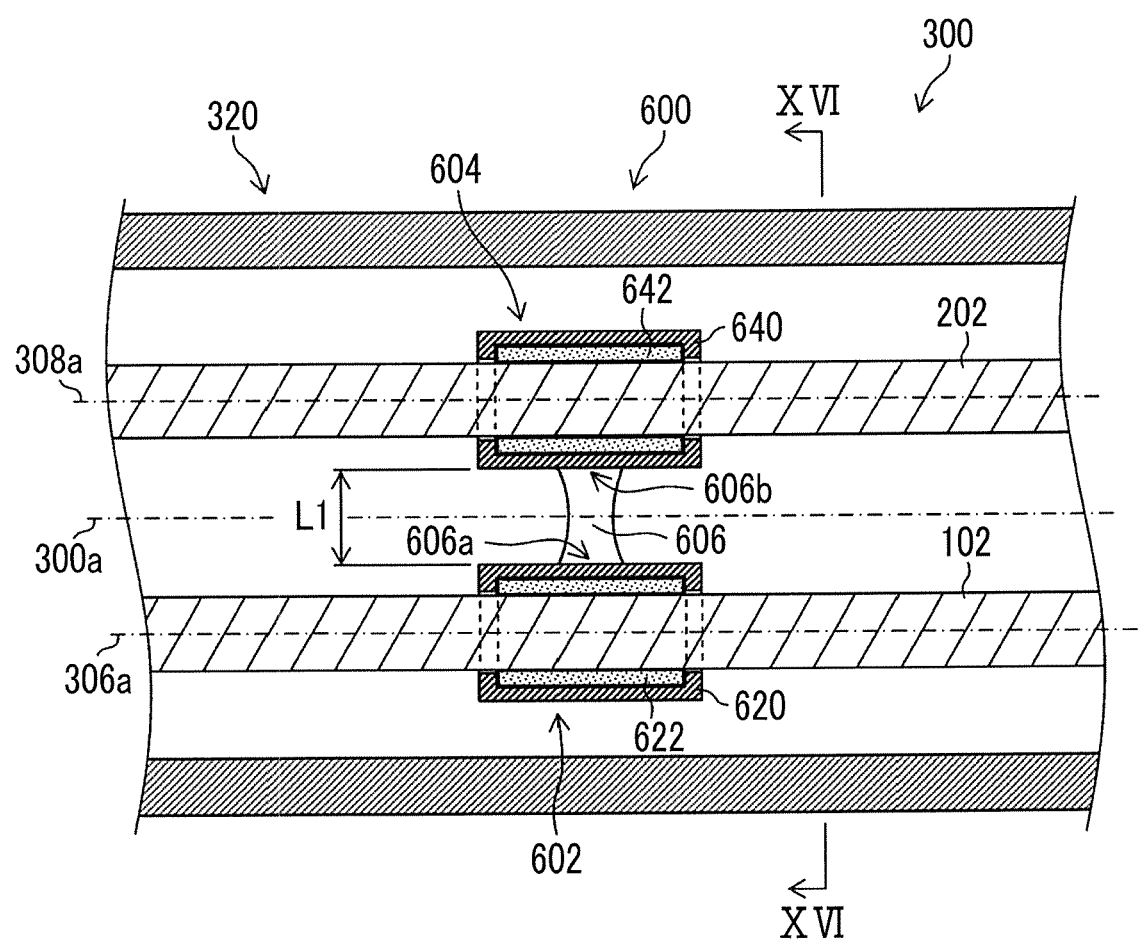
FIG. 15 is an enlarged view illustrating a peripheral part of the interlocking member in FIG. 14 in an enlarged manner.

FIG. 14 is a cross-sectional view illustrating the configuration of an interlocking member 600 of the embodiment of the invention in a cross section of the overtube 300 cut along the reference axis 300a, and FIG. 15 is an enlarged view illustrating a peripheral part of the interlocking member 600 in FIG. 14 in an enlarged manner. Additionally, FIG. 16 is a cross-sectional view when viewed from arrow XVI-XVI in FIG. 15.

In addition, in the overtube 300 in which the interlocking member 600 of the present embodiment is built, the same reference signs are given to members having functions that are the same as or similar to those of the overtube 300 in which the slider 400 of the above reference form is built. Additionally, FIG. 15 illustrates a state where the endoscope insertion part 102 and the treatment tool insertion part 202 are inserted through the endoscope insertion passage 306 and the treatment tool insertion passage 308 of the overtube 300.

As illustrated in these drawings, the interlocking member 600 has a first sleeve 602 serving as a first holding part holding the endoscope insertion part 102 inserted through the endoscope insertion passage 306 of the overtube 300, a second sleeve 604 serving as a second holding part holding the treatment tool insertion part 202 inserted through the treatment tool insertion passage 308 of the overtube 300, and a coupling member 606 that couples the second sleeve 604 and the first sleeve 602 together.

Figure 16:
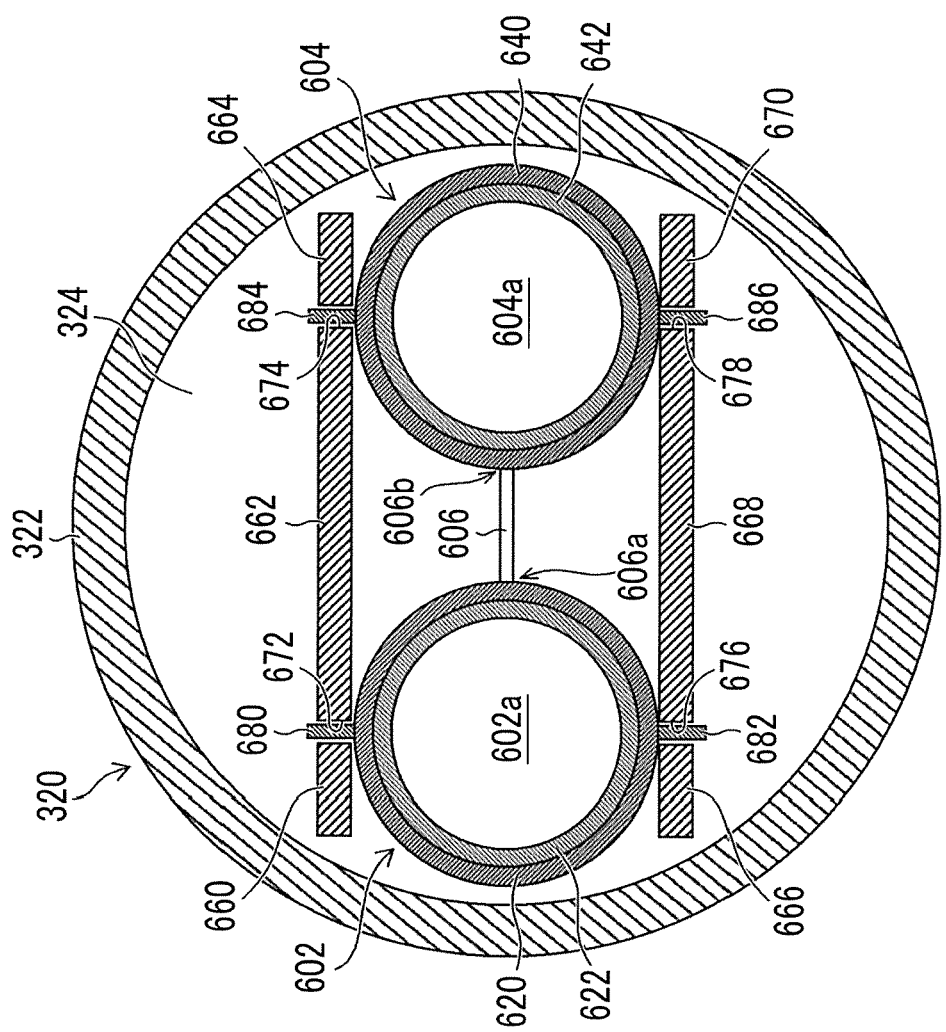
FIG. 16 is a cross-sectional view when viewed from arrow XVI-XVI in FIG. 15.

The first sleeve 602, for example, has a sleeve body 620 that is a frame configured similar to the sleeve 440 in the slider 400 of the above reference form, for example, and formed in a cylindrical shape as illustrated in FIGS. 15 and 16, and a pressure-contact member 622 that is fixed inside the sleeve body 620 and formed in a cylindrical shape using an elastic material.

Similarly, the second sleeve 604 also has a sleeve body 640 that is a frame formed in a cylindrical shape as illustrated in FIGS. 15 and 16, and a pressure-contact member 642 that is fixed inside the sleeve body 640 and formed in a cylindrical shape using an elastic material.

Additionally, as illustrated in FIG. 16, in an upper part and a lower part of the inside (the inside of a long tubular overtube body 320) of the overtube 300, similar to the guide grooves 370 and 372 formed by the guide plates 374 and 374 and the guide plates 376 and 376 illustrated in FIG. 6, guide plates 660, 662, and 664 and guide plates 666, 668, and 670 that extend in the direction of the reference axis 300a are stretched between the proximal end cap 340 and the distal end cap 360, and guide grooves 672 and 674 and guide grooves 676 and 678 that extend in the direction of the reference axis 300a is formed by the guide plates 660, 662, and 664 and the guide plates 666, 668, and 670.

Meanwhile, protruding strips 680 and 682 that extend in the direction (forward-backward direction) of the axis 300a are formed at an upper part and a lower part of an outer peripheral surface of the first sleeve 602 (sleeve body 620).

The protruding strips 680 and 682 are respectively fitted into the guide grooves 672 and 676, and are disposed in a state where the outer peripheral surface of the first sleeve 602 has contacted or approached the guide plates 660, 662, 666, and 668.

Similarly, protruding strips 684 and 686 that extend in the direction (forward-backward direction) of the axis 300a are formed at an upper part and a lower part of an outer peripheral surface of the second sleeve 604 (sleeve body 640).

The protruding strips 684 and 686 are respectively fitted into the guide grooves 674 and 678, and are disposed in a state where the outer peripheral surface of the second sleeve 604 has contacted or approached the guide plates 662, 664, 668, and 670.

Accordingly, the first sleeve 602 has its central axis disposed substantially coaxially with the endoscope insertion axis 306a and is supported so as to be movable forward and backward in the forward-backward direction and so as not to be rotatable around its central axis.

Additionally, the second sleeve 604 has its central axis disposed substantially coaxially with the treatment tool insertion axis 308a and is supported so as to be movable forward and backward in the forward-backward direction and so as not to be rotatable around its central axis.

In addition, the mechanism that supports the first sleeve 602 and the second sleeve 604 so as to be movable forward and backward in the direction of the reference axis 300a of the overtube 300 may be different from that of the present embodiment.

According to such first sleeve 602 and the second sleeve 604, when the endoscope insertion part 102 is inserted through the endoscope insertion passage 306 as illustrated in FIG. 15, the endoscope insertion part 102 is inserted through a through-hole 602a (the through-hole 602a on an inner peripheral side of the pressure-contact member 622, refer to FIG. 16) of the first sleeve 602, and the pressure-contact member 622 is brought into pressure contact with (engaged with) the outer peripheral surface of the endoscope insertion part 102. Accordingly, the first sleeve 602 and the endoscope insertion part 102 are coupled together.

Additionally, as illustrated in FIG. 15, when the treatment tool insertion part 202 is inserted through the treatment tool insertion passage 308, the treatment tool insertion part 202 is inserted through a through-hole 604a (the through-hole 604a on an inner peripheral side of the pressure-contact member 642, refer to FIG. 16) of the second sleeve 604, and the pressure-contact member 642 is brought into pressure contact with (engaged with) the outer peripheral surface of the treatment tool insertion part 202. Accordingly, the second sleeve 604 and the treatment tool insertion part 202 are coupled together.

In addition, since the coupling between the first sleeve 602 and the endoscope insertion part 102 and the coupling between the second sleeve 604 and the treatment tool insertion part 202, which are described herein, are based on the elastic forces of the pressure-contact members 622 and 642, the position of the endoscope insertion part 102 where the first sleeve 602 is coupled, and the position of the treatment tool insertion part 202 where the second sleeve 604 is coupled can be arbitrarily adjusted.

As illustrated in FIGS. 15 and 16, the coupling member 606 has one first end part 606a fixed to the first sleeve 602 serving as a first fixing part and the other second end part 606b fixed to the second sleeve 604 serving as a second fixing part, and has an elastic body between the first end part 606a and the second end part 606b. The elastic body includes, for example, members using the elastic force of rubber, a spring, and metal, members using the elasticity of resin such as plastic, members using the elastic force of air, and the like.

Additionally, the first end part 606a is fixed to, for example, a right side part of the outer peripheral surface of the first sleeve 602 in the vicinity of the center thereof in the forward-backward direction, and the second end part 606b is fixed to, for example, a left side part of the outer peripheral surface of the second sleeve 604 in the vicinity of the center thereof in the forward-backward direction.

However, a first fixed position in the first sleeve 602 to which the first end part 606a is fixed, and a second fixed position in the second sleeve 604 to which the second end part 606b is fixed are not limited to specific positions.

The coupling member 606 changes in an elastic state according to the relative movement of the first sleeve 602 and the second sleeve 604 in the forward-backward direction, and increases a tensile force between the first end part 606a and the second end part 606b as the coupling members is stretched and becomes longer.

According to such a coupling member 606, the coupling member 606 has a reference state where a tensile force in the direction (forward-backward direction) of the reference axis 300a is not caused between the first sleeve 602 and the second sleeve 604 in a case where the positions of the first end part 606a and the second end part 606b of the coupling member 606 in the forward-backward direction coincide with each other.

Here, a distance between the first end part 606a and the second end part 606b in a case where the coupling member 606 is in the reference state is represented by L1 as the natural length, and this state is referred to as a state where the coupling member 606 has the natural length L1. However, the natural length L1 herein does not necessary indicate the length in a case where no load is applied to the coupling member 606, and may be in a state where a tensile force acts between the first end part 606a and the second end part 606b in a case where the coupling member 606 is in the state of the natural length L1.

Meanwhile, a distance between the first end part 606a and the second end part 606b when the relative movement of the first sleeve 602 and the second sleeve 604 in the forward-backward direction has occurred with respect to a state where the coupling member 606 has the natural length L1 depending on the forward and backward movement of the second sleeve 604 with respect to the overtube 300, or the like, is repressed by L2, and this state is referred to as a state where the coupling member 606 has the length L2.

In this case, the coupling member 606 generate a force of biasing the first end part 606a and the second end part 606b in a direction in which these end parts are brought close to each other in the direction (forward-backward direction) of the reference axis 300a of the overtube 300, in a case where L2 becomes longer than L1.

Additionally, in the coupling member 606, the force of biasing the first end part 606a and the second end part 606b in the direction in which these end parts are brought close to each other in the forward-backward direction becomes larger as L2 becomes longer than L1.

Hence, as the movement distance of the relative movement of the first sleeve 602 and the second sleeve 604 in the forward-backward direction with respect to a state where the coupling member 606 has the natural length L1 is larger, that is, as a difference between the length L2 and the natural length L1 of the coupling member 606 is larger, the response of the interlocking of the first sleeve 602 with respect to the movement of the second sleeve 604 in the forward-backward direction (the followability of the first sleeve 602 with respect to the movement of the second sleeve 604 in the forward-backward direction) becomes quicker. On the contrary, as the movement distance is smaller, that is, as the difference between the length L2 and the natural length L1 of the coupling member 606 are smaller, the response becomes slower.

Here, the response of the interlocking of the first sleeve 602 with respect to the movement of the second sleeve 604 in the forward-backward direction (hereinafter referred to as the response of the first sleeve 602 with respect to the second sleeve 604) becomes slower as a resistance force that hinders the movement of the first sleeve 602 in the forward-backward direction and is received from other than the coupling member 606 is larger.

Thus, the overtube 300 is provided with a resistance force generating part for generating such a resistance force in order to moderately delay the response of the overtube 300.

Figure 17:
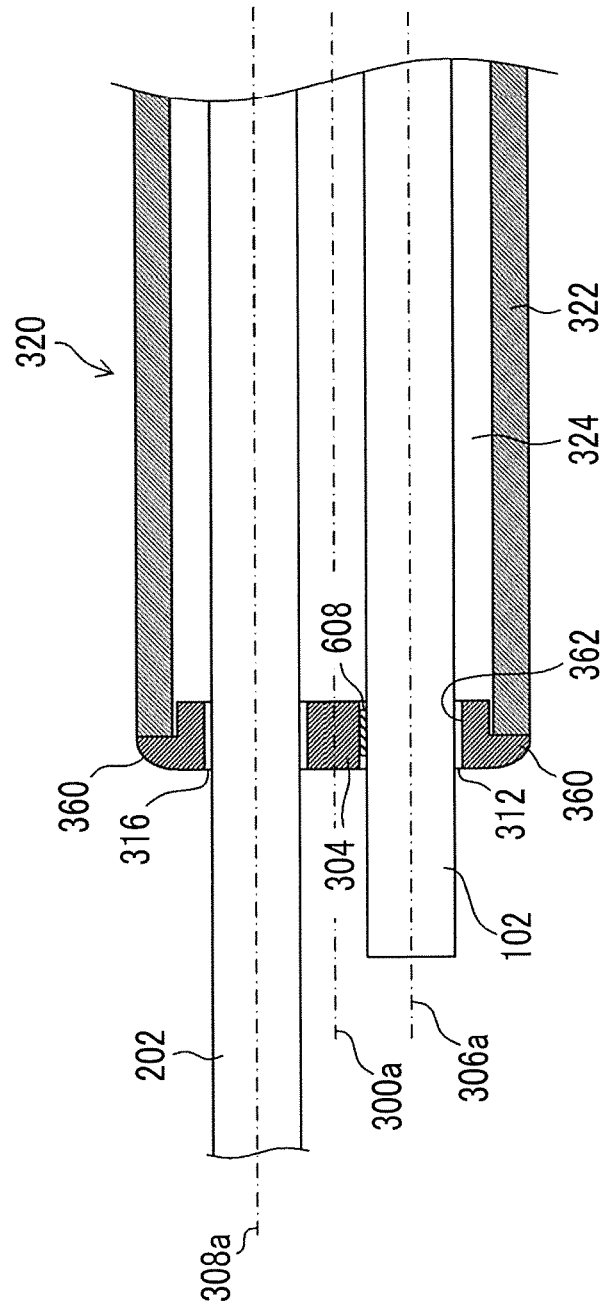
FIG. 17 is a cross-sectional view illustrating a resistance force generating part.

For example, as illustrated in FIG. 17, a resistance force generating part 608 is provided in the through-hole 362 (the through-hole 362 of the distal end cap 360) in the vicinity of the first distal end opening 312 of the overtube 300 where the endoscope insertion part 102 is delivered from the overtube 300.

The resistance force generating part 608 is formed of, for example, a friction body, and is provided so as to contact the endoscope insertion part 102, which is inserted through the endoscope insertion passage 306 and to which the first sleeve 602 is coupled, partially or entirely in the circumferential direction.

Accordingly, when the endoscope insertion part 102 has moved in the forward-backward direction together with the first sleeve 602, the endoscope insertion part 102 slides on the resistance force generating part 608 and receives a resistance force resulting from friction. Then, the resistance force is applied to the first sleeve 602 via the endoscope insertion part 102.

Additionally, the magnitude of the resistance force generated by the resistance force generating part 608 can be adjusted depending on the contact area between the resistance force generating part 608 and the endoscope insertion part 102, or the like, and is adjusted such that the response of the first sleeve 602 with respect to the second sleeve 604 becomes suitable by adjusting the magnitude of the resistance force.

In addition, in the present embodiment, as an example, the resistance force generating part is constituted of the friction body. However, the resistance force generating part is not limited to this, and may be constituted of, for example, a viscous body like a dash pot, a combination thereof, or the like.

Additionally, such a resistance force generating part is provide in an arbitrary portion between a member constituting the overtube 300 and the endoscope insertion part 102 through which the overtube 300 is inserted or between the member constituting the overtube 300 and the first sleeve 602, and may not be a special constituent element added in order to generate the resistance force.

For example, as illustrated in FIG. 14, the endoscope insertion passage 306 of the overtube 300 is provided with a valve member 346 (a valve member 346 in the proximal end cap 340) that secures the airtightness of the internal space of the overtube 300. Since the valve member 346 slides on the endoscope insertion part 102, this valve member can be the resistance force generating part.

Additionally, as illustrated in FIG. 16, the outer peripheral surface of the first sleeve 602 (an outer peripheral surface of the sleeve body 620) is disposed in a state where this outer peripheral surface has contacted or approached inner peripheral surfaces of the guide plates 660, 662, 666, and 668 of the long tubular overtube body 320. Hence, the outer peripheral surface of the first sleeve 602 can be provided with the resistance force generating part that contacts any of the long tubular overtube body 320 and the guide plates 660, 662, 666, and 668.

Moreover, it is possible to adopt an aspect the resistance force generating part(s) is (are) provided to either one or both of the first sleeve 602 and the second sleeve 604. In a case where the resistance force generating parts are provided to both the first sleeve 602 and the second sleeve 604, the response of the second sleeve 604 with respect to the first sleeve 602 when the endoscope insertion part 102 moves forward and backward can also be adjusted, similar to the response of the first sleeve 602 with respect to the second sleeve 604.

The working of the interlocking member 600 of the embodiment of the invention as above will be described.

Figure 20:
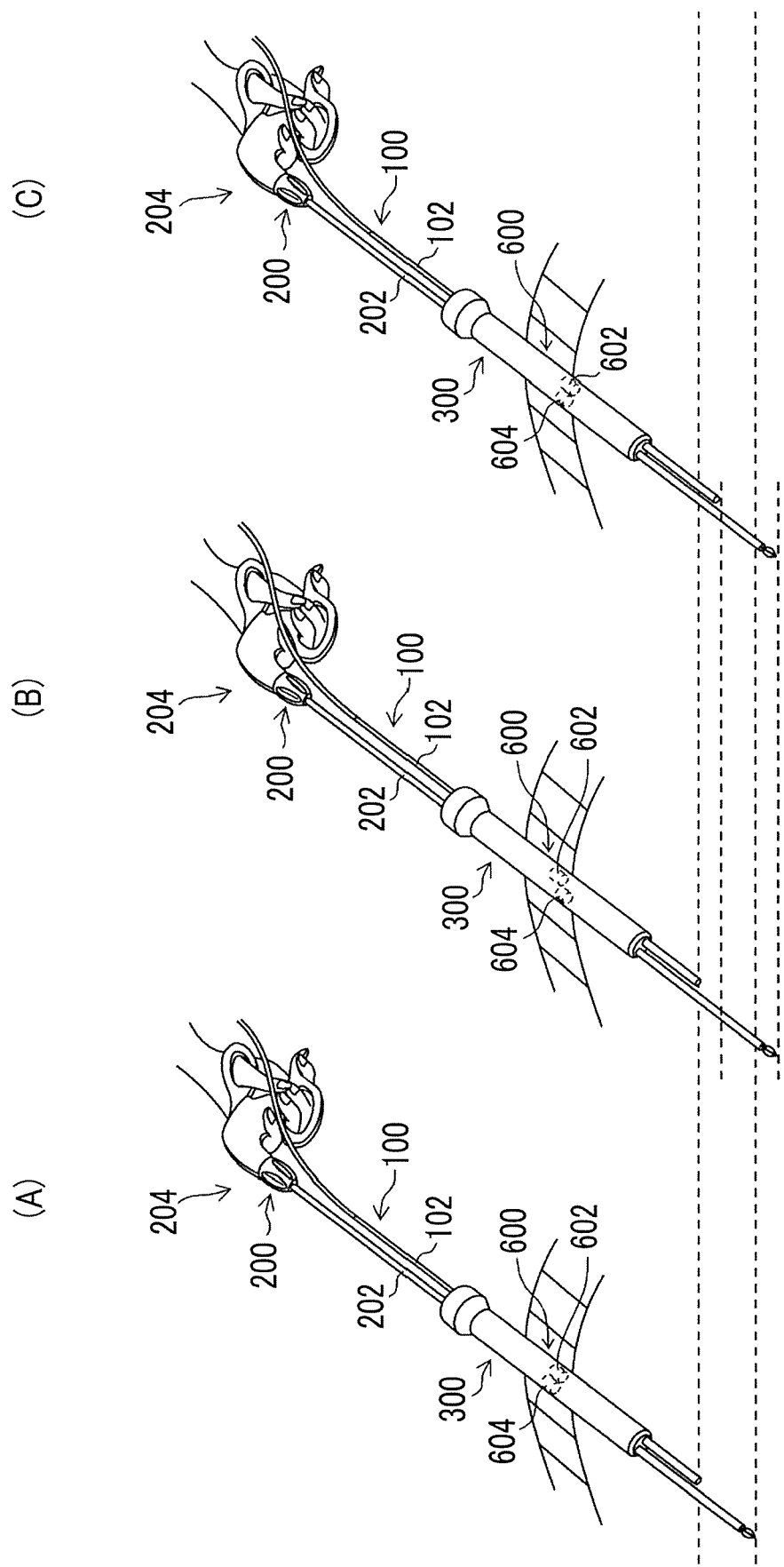
FIG. 20 is an explanatory view used for the description of the working of the interlocking member of the embodiment of the invention, portion (A) illustrates a state where a coupling member has natural length, portion (B) illustrates a state immediately after the treatment tool insertion part is moved forward on a small scale, and portion (C) illustrates a state after the treatment tool insertion part is stopped and held after the forward movement.

Similar to portion (A) of FIG. 12 illustrated in the overtube 300 on which the slider 400 is mounted, as illustrated in portion (A) of FIG. 20, after the overtube 300 on which the interlocking member 600 of the present embodiment is mounted is inserted into a patient's body wall and a pneumoperitoneum gas is injected into a body cavity, the endoscope 100 (endoscope insertion part 102) and the treatment tool 200 (treatment tool insertion part 202) are respectively inserted into the endoscope insertion passage 306 and the treatment tool insertion passage 308 of the overtube 300, and the endoscope insertion part 102 and the treatment tool insertion part 202 are mounted on the overtube 300.

In this case, the endoscope insertion part 102 is coupled to the first sleeve 602, and the treatment tool insertion part 202 is coupled to the second sleeve 604.

Then, it is assumed that the state of the interlocking member 600 in portion (A) of FIG. 20 is the state where the positions of the first end part 606a and the second end part 606b of the coupling member 606 in the forward-backward direction substantially coincide with each other as illustrated in FIG. 15, that is, a state where the coupling member 606 has the natural length L1.

In this case, in a case where the treatment tool insertion part 202 is minutely moved forward with the hand that a surgeon is gripping the operating part 204 of the treatment tool 200, immediately after the minute movement, the difference between the length L2 and the natural length L1 of the coupling member 606 is small and the response of the first sleeve 602 with respect to the second sleeve 604 is slow. Therefore, a state where the first sleeve 602 has substantially stopped with respect to the overtube 300 is brought about.

Figure 18:
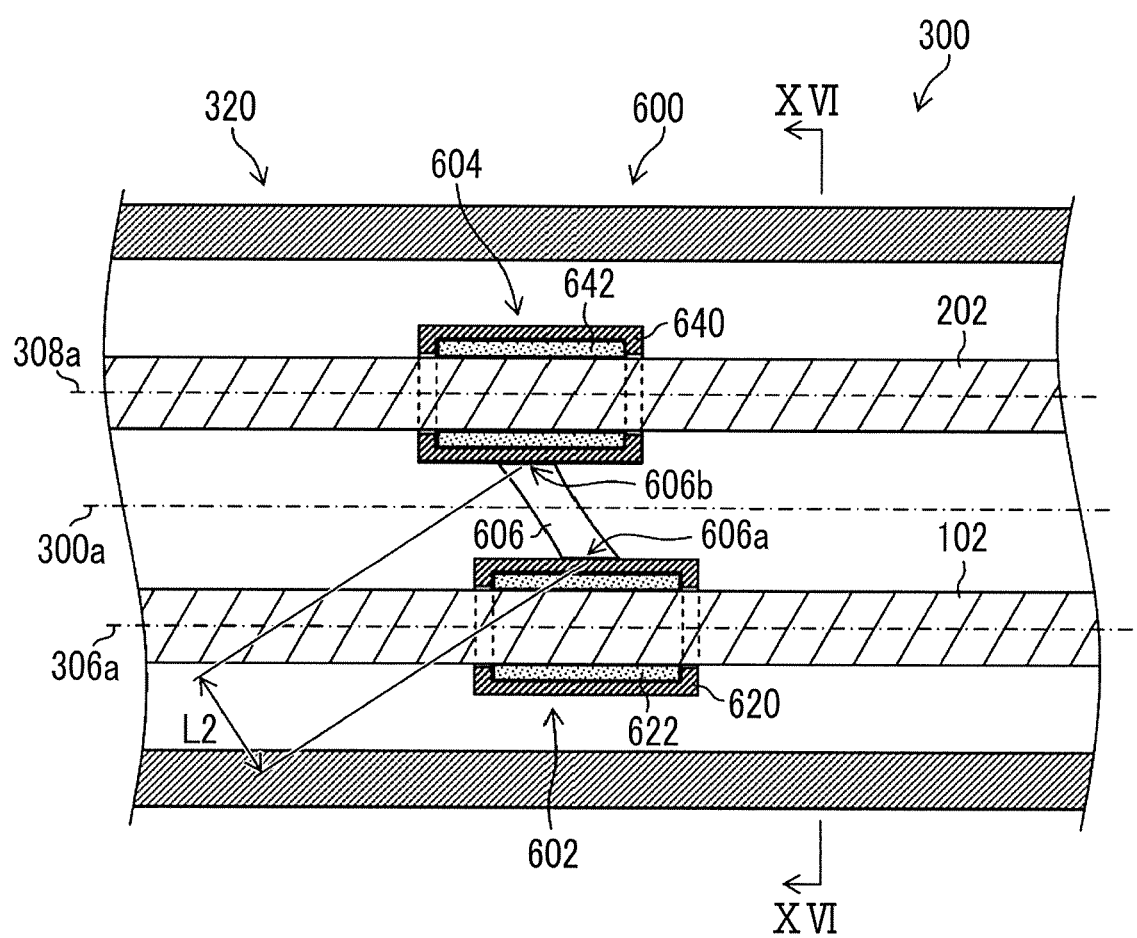
FIG. 18 is an explanatory view used for the description of the working of the interlocking member of the embodiment of the invention.

Then, as illustrated in FIG. 18, the coupling member 606 is stretched due to the forward movement of the second sleeve 604, and the first sleeve 602 moves backward relative to the second sleeve 604. That is, the difference between the length L2 and the natural length L1 of the coupling member 606 becomes gradually large.

Hence, immediately after the forward movement of the treatment tool insertion part 202 (the second sleeve 604), as illustrated in portion (B) of FIG. 20, only the treatment tool insertion part 202 moves forward in a state where the endoscope insertion part 102 has substantially stopped.

In this way, in a case where the surgeon subsequently holds the treatment tool insertion part 202 in the stopped state after the treatment tool insertion part 202 is minutely moved forward, the first sleeve 602 moves forward in the direction in which the first end part 606a and the second end part 606b of the coupling member 606 approach each other due to the tensile force of the coupling member 606, that is, such that the difference between the length L2 and the natural length L1 of the coupling member 606 reaches zero.

Then, as illustrated in FIG. 15, in a case where the state where the positions of the first end part 606a and the second end part 606b of the coupling member 606 in the forward-backward direction substantially coincide with each other, that is, the state where the coupling member 606 has the natural length L1 is brought about, the forward movement of the first sleeve 602 stops.

Hence, while the surgeon holds the treatment tool insertion part 202 in the stopped state, only the endoscope insertion part 102 moves forward, and in a case where a relative positional relationship between the endoscope insertion part 102 and the treatment tool insertion part 202 as illustrated in portion (C) of FIG. 20 is brought into the same state as portion (A) of FIG. 20, the forward movement of the endoscope insertion part 102 stops.

In addition, although description is omitted, the operation even when the surgeon has minutely moved backward the treatment tool insertion part 202 is also the same as that when the treatment tool insertion part 202 is minutely moved forward.

In this way, the interlocking member 600 forms a low response region where the endoscope insertion part 102 does not temporarily interlock with the minute forward and backward movement operation of the treatment tool insertion part 202.

In contrast, similar to the state of portion (A) of FIG. 20, it is assumed that the interlocking member 600 is in the state where the positions of the first end part 606a and the second end part 606b of the coupling member 606 in the forward-backward direction substantially coincide with each other as illustrated in FIG. 15, that is, the state where the coupling member 606 has the natural length L1.

Also, it is assumed that the treatment tool insertion part 202 is largely moved forward with the hand that the surgeon is gripping the operating part 204 of the treatment tool 200.

In this case, in an initial stage where the movement distance of the forward movement of the treatment tool insertion part 202 is small, similar to the above-described case where the treatment tool insertion part 202 is minutely moved forward, the difference between the length L2 and the natural length L1 of the coupling member 606 is small and the response of the first sleeve 602 with respect to the second sleeve 604 is slow. Therefore, a state where the first sleeve 602 has substantially stopped with respect to the overtube 300 is brought about.

Then, as illustrated in FIG. 18, the coupling member 606 is stretched due to the forward movement of the second sleeve 604, and the first sleeve 602 moves backward relative to the second sleeve 604 from the first position. That is, the difference between the length L2 and the natural length L1 of the coupling member 606 becomes gradually large.

Subsequently, in a case where the forward movement of the treatment tool insertion part 202 continues and the movement distance thereof becomes large, the coupling member 606 is further stretched, and the difference between the length L2 and the natural length L1 of the coupling member 606 becomes larger. Accordingly, the tensile force of the coupling member 606 becomes gradually large, and the response of the first sleeve 602 with respect to the second sleeve 604 becomes gradually quick.

Figure 19:
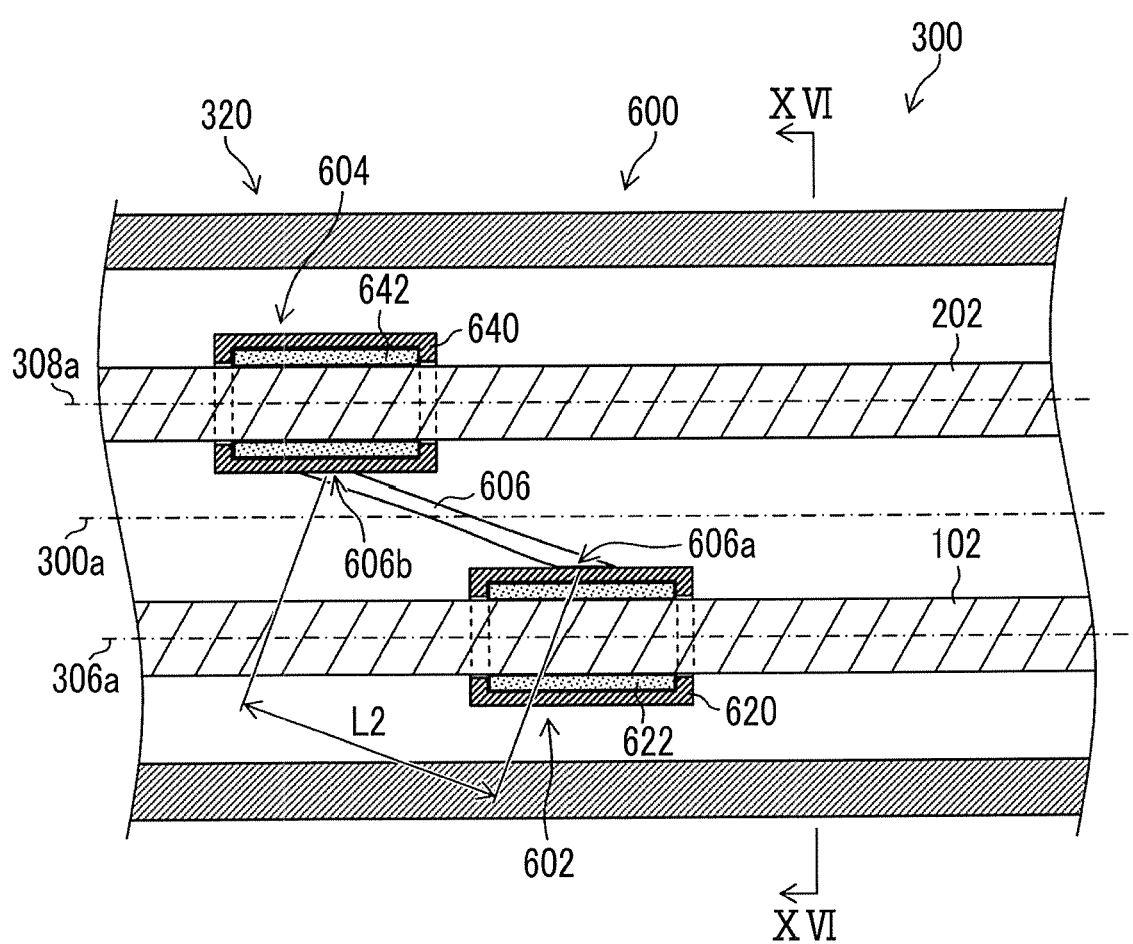
FIG. 19 is an explanatory view used for the description of the working of the interlocking member of the embodiment of the invention.

Then, as illustrated in FIG. 19, when the difference between the length L2 and the natural length L1 of the coupling member 606 becomes large to some extent large, the first sleeve 602 starts the forward movement thereof to the overtube 300, and the first sleeve 602 also moves forward together with the forward movement of the second sleeve 604.

Figure 21:
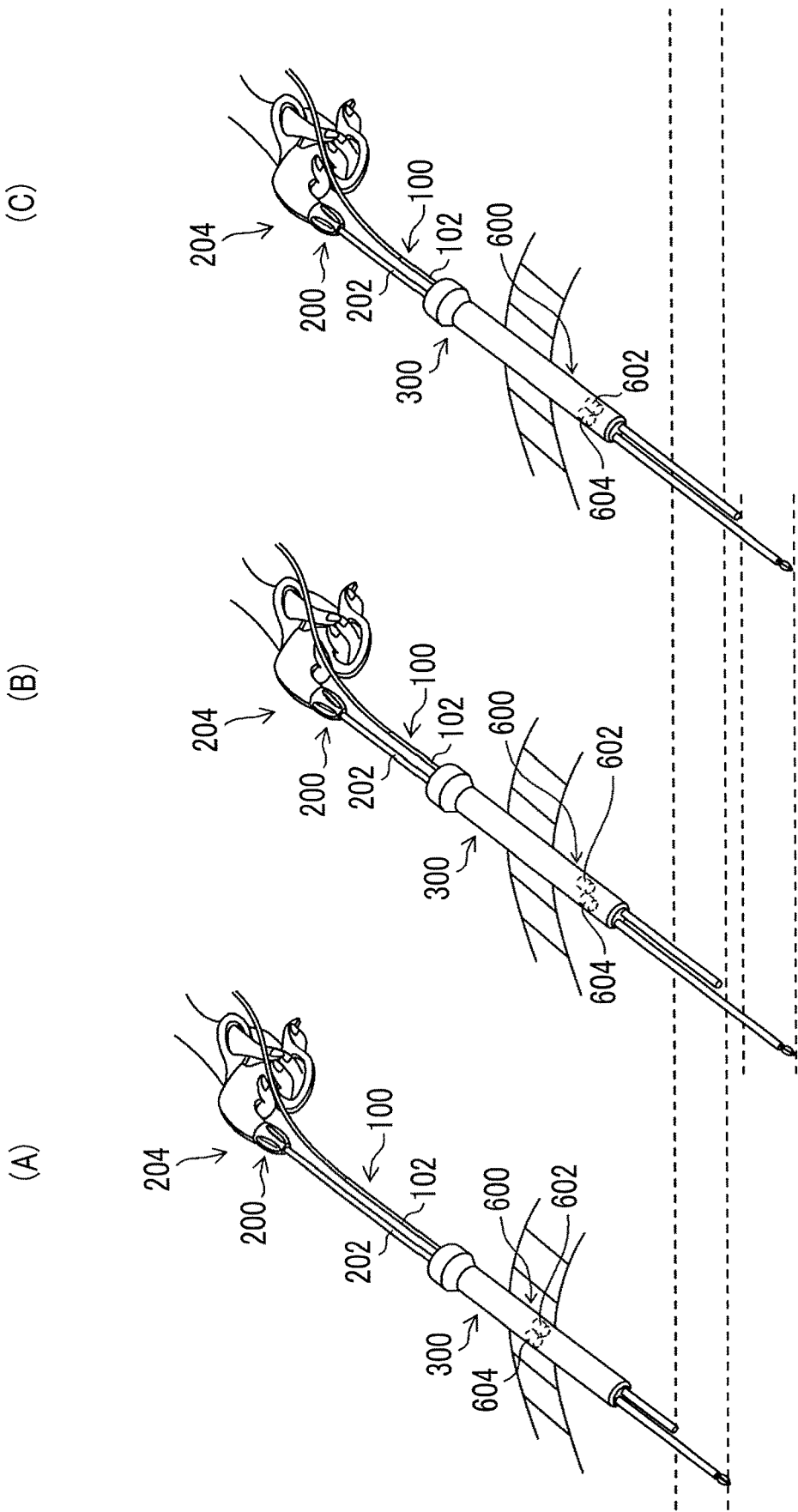
FIG. 21 is an explanatory view used for the description of the working of the interlocking member of the embodiment of the invention, portion (A) illustrates a state where a coupling member has natural length, portion (B) illustrates a state immediately after the treatment tool insertion part is largely moved forward, and portion (C) illustrates a state after the treatment tool insertion part is stopped and held after the forward movement.

Hence, during the large forward movement of the treatment tool insertion part 202 (second sleeve 604), as illustrated in portion (B) of FIG. 21 with respect to the state of portion (A) of FIG. 21 illustrating the same state as portion (A) of FIG. 20, the endoscope insertion part 102 moves forward together with the treatment tool insertion part 202 after only the treatment tool insertion part 202 minutely has moved forward in a state where the endoscope insertion part 102 has substantially stopped.

In this way, in a case where the surgeon subsequently holds the treatment tool insertion part 202 in the stopped state after the treatment tool insertion part 202 has been largely stopped, the first sleeve 602 continues moving forward due to the tensile force of the coupling member 606, and in a case where the state where the positions of the first end part 606a and the second end part 606b of the coupling member 606 in the forward-backward direction substantially coincide with each other as illustrated in FIG. 15, that is, the state where the coupling member 606 has the natural length L1 is brought about, the forward movement of the first sleeve 602 stops.

Hence, while the treatment tool insertion part 202 is held in the stopped state, only the endoscope insertion part 102 moves forward, and in a case where the relative positional relationship between the endoscope insertion part 102 and the treatment tool insertion part 202 as illustrated in portion (C) of FIG. 21 is brought into the same state as portion (A) of FIG. 21, the forward movement of the endoscope insertion part 102 stops.

In addition, although description is omitted, the operation even when the surgeon has largely moved backward the treatment tool insertion part 202 is also the same as that when the treatment tool insertion part 202 is largely moved forward.

In this way, the interlocking member 600 forms a high response region where the endoscope insertion part 102 is interlocked with the forward and backward movement operation of the treatment tool insertion part 202 exceeding the low response region.

According to the working of the above interlocking member 600, effects similar to the slider 400 of the above reference form are exhibited.

That is, in a case where the displacement of the treatment tool insertion part 202 in the axial direction is large (in a case where a large amplitude of forward and backward movement operation has been performed) when a surgeon has moved the treatment tool insertion part 202 forward and backward in the axial direction, the endoscope insertion part 102 also moves forward and backward in an interlocking manner in the forward-backward direction, in the upward-downward direction, and in the rightward-leftward direction. Thus, the visual field, orientation, and the like of the endoscope 100 can be changed as intended by a surgeon. Additionally, the visual field is always given to pick up an image of the distal end site of the treatment tool 200 and consequently, an image that is optimal for treatment is automatically provided. In a case where it is desired to check sites other than a site to be treated, the checking can be performed by moving the treatment tool insertion part 202, and a surgeon can perform operations as desired.

Hence, an assistant (endoscopic technician) who operates the endoscope 100 apart from the surgeon can be made unnecessary, and a troublesome condition in which the surgeon should instruct an assistant about the visual field, orientation, and the like of the endoscope 100 serially can be eliminated.

Additionally, in a case where the displacement of the treatment tool insertion part 202 in the axial direction is small (in a case where a small amplitude of forward and backward movement operation has been performed), the endoscope insertion part 102 does not interlock temporarily. Therefore, while the small-amplitude of forward and backward operation continues, the endoscope insertion part 102 does not move and thus an endoscopic image can be prevented from fluctuating unnecessarily, a sense of perspective can be suitably maintained, and a stable endoscopic image can be provided.

Moreover, since the interlocking member 600 of the embodiment of the invention has a simpler configuration than a case where the interlocking member is the above slider 400, cost reduction, simplification in configuration, reduction in diameter, and the like of the overtube 300 can be achieved.

As described above, in the interlocking member 600 of the embodiment of the invention, as illustrated in FIG. 15, the coupling member 606 couples the first sleeve 602 and the second sleeve 604 together in the direction orthogonal to the reference axis 300a. However, the coupling member 606 is not limited to this.

Figure 22:
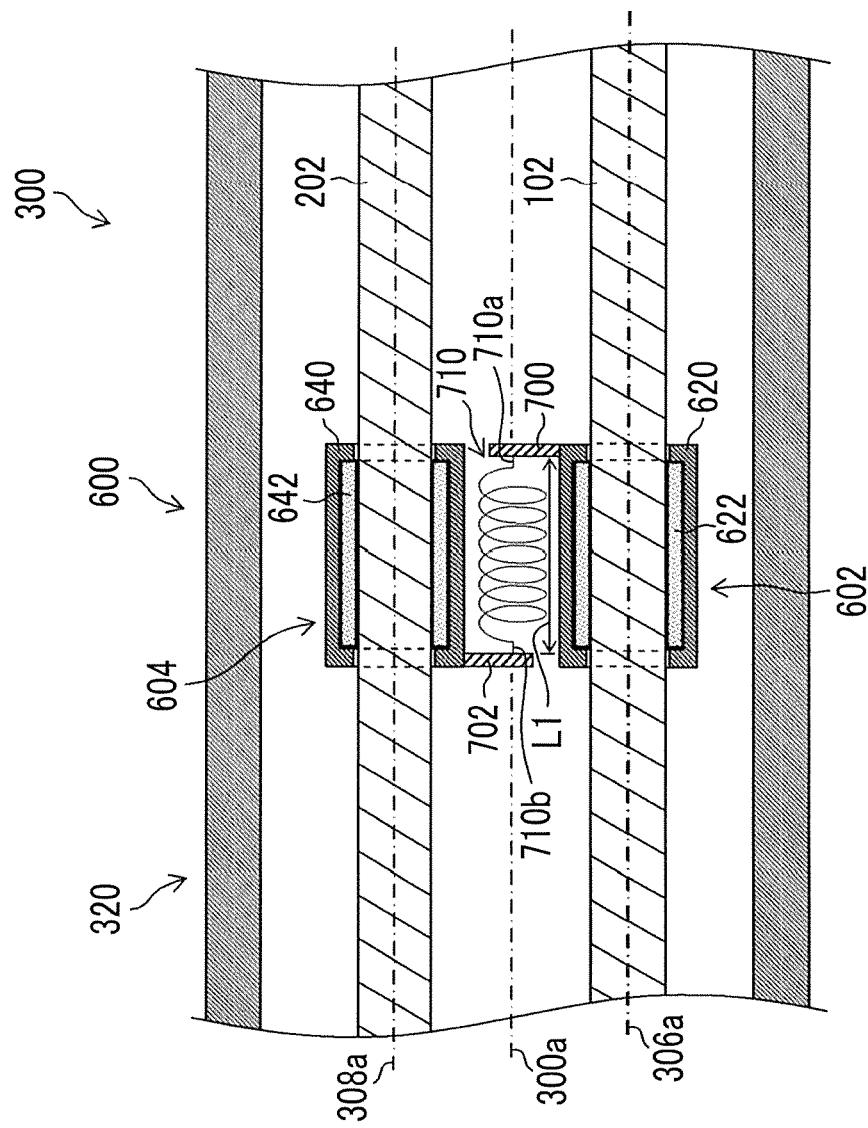
FIG. 22 is a view illustrating another embodiment of the coupling member in the interlocking member of the embodiment of the invention.

For example, as illustrated in FIG. 22, a support part 700 provided to protrude from the first sleeve 602 and a support part 702 provided to protrude from the second sleeve 604 may be coupled together by a coupling member 710 in the direction of the reference axis 300a. A first end part 710a that is one end part of the coupling member 710 and is the first fixing part is fixed to the first sleeve 602 via the support part 700, and a second end part 710b that is the other end part of the coupling member 710 and is the second fixing part is fixed to the second sleeve 604 via the support part 702.

The coupling member 710 is, for example, a coil spring, and is brought into the reference state where a force in the direction (forward-backward direction) of the reference axis 300a is not caused between the first sleeve 602 and the second sleeve 604 in the state of the natural length L1 where the coil spring is not expanded and compressed as illustrated in this drawing.

According to this, exactly the same working effects as those of the interlocking member 600 by the above coupling member 606 are exhibited.

That is, a distance between the first end part 710a and the second end part 710b when the relative movement of the first sleeve 602 and the second sleeve 604 in the forward-backward direction has occurred with respect to a state where the coupling member 710 has the natural length L1 depending on the forward and backward movement of the second sleeve 604 with respect to the overtube 300, or the like, is repressed by L2, and this state is referred to as a state where the coupling member 710 has the length L2.

Figure 23:
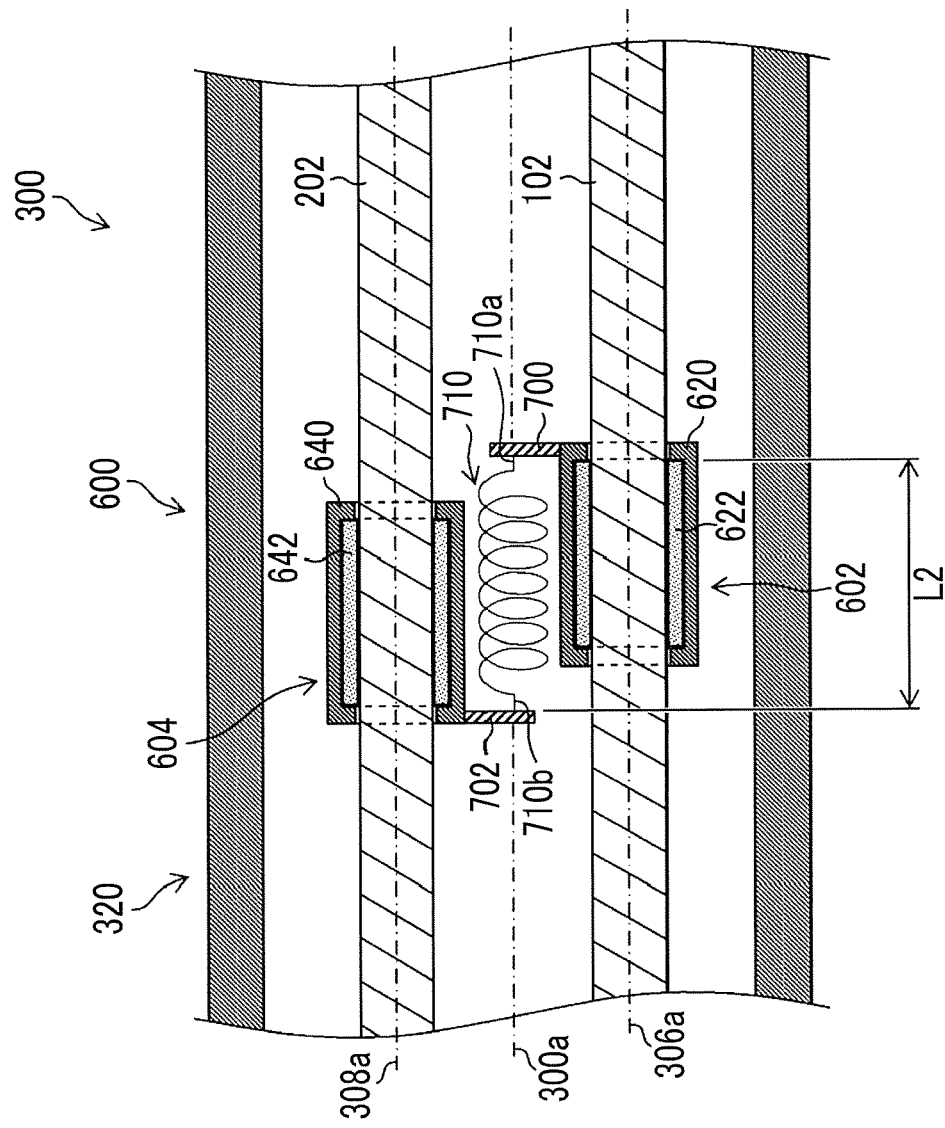
FIG. 23 is a view illustrating a state where the coupling member of FIG. 22 is stretched from the natural length.

In this case, as illustrated in FIG. 23, the coupling member 710 generate a force of biasing the first end part 710a and the second end part 710b in a direction in which these end parts are brought close to each other in the direction (forward-backward direction) of the reference axis 300a of the overtube 300, in a case where L2 becomes longer than L1.

Additionally, in the coupling member 710, the force of biasing the first end part 710a and the second end part 710b in the direction in which these end parts are brought close to each other in the forward-backward direction becomes larger as L2 becomes longer with respect to L1.

Figure 24:
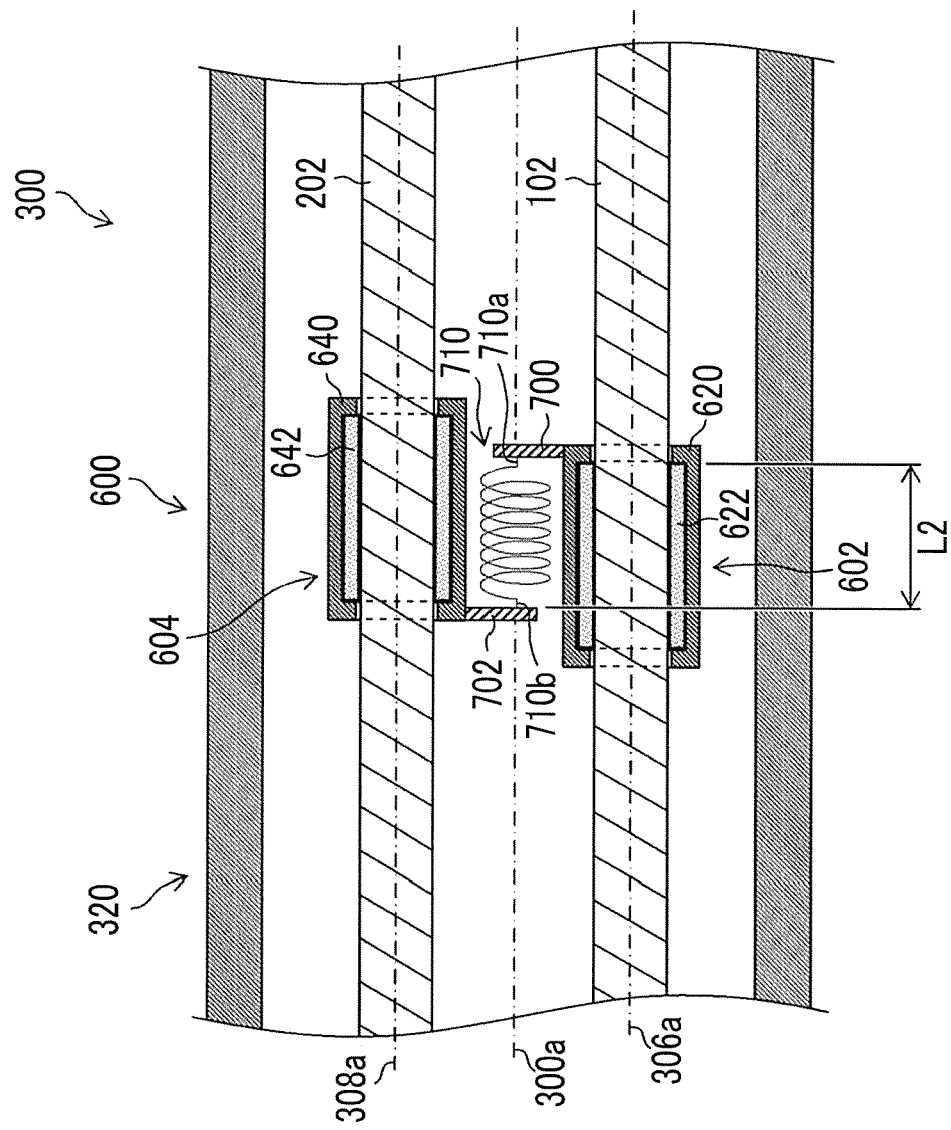
FIG. 24 is a view illustrating a state where the coupling member of FIG. 22 is compressed from the natural length.

On the other hand, as illustrated in FIG. 24, the coupling member 710 generate a force of biasing the first end part 710a and the second end part 710b in a direction in which these end parts are moved away from each other in the direction (forward-backward direction) of the reference axis 300a of the overtube 300, in a case where L2 becomes shorter than L1.

Additionally, in the coupling member 710, the force of biasing the first end part 710a and the second end part 710b in the direction in which these end parts are moved away from each other in the forward-backward direction becomes larger as L2 becomes shorter than L1.

Hence, similar to the interlocking member 600 based on the above coupling member 606, Hence, as the movement distance of the relative movement of the first sleeve 602 and the second sleeve 604 in the forward-backward direction with respect to a state where the coupling member 710 has the natural length L1 is larger, that is, as a difference between the length L2 and the natural length L1 of the coupling member 710 is larger, the response of the interlocking of the first sleeve 602 with respect to the movement of the second sleeve 604 in the forward-backward direction becomes quicker. On the contrary, as the movement distance are smaller, that is, as the difference between the length L2 and the natural length L1 of the coupling member 710 are smaller, the response becomes slower.

In addition, any of the support part 700 of the first sleeve 602 and the support part 702 of the second sleeve 604 may be disposed on the front side.

Additionally, in the interlocking member 600 of the embodiment of the invention, the rotation of the first sleeve 602 and the second sleeve 604 around their respective central axes, and the rotation of the endoscope insertion part 102 is restricted and the treatment tool insertion part 202 coupled to these sleeves around their axes is also restricted. In contrast, any one or both of the endoscope insertion part 102 and the treatment tool insertion part 202 around its axis may be rotatable.

For example, it is preferable that the rotation the treatment tool insertion part 202 around its axis is possible. In that case, the second sleeve 604 may be configured as illustrated in a cross-sectional view of FIG. 25. In this drawing, the second sleeve 604 is constituted of the above-described cylindrical sleeve body 640, a cylindrical intermediate frame 720 that is rotatably supported around its central axis with respect to the sleeve body 640 on the inner peripheral side of the sleeve body 640, and the above-described cylindrical pressure-contact member 642 that is fixed to the inner peripheral side of the intermediate frame 720.

Figure 25:
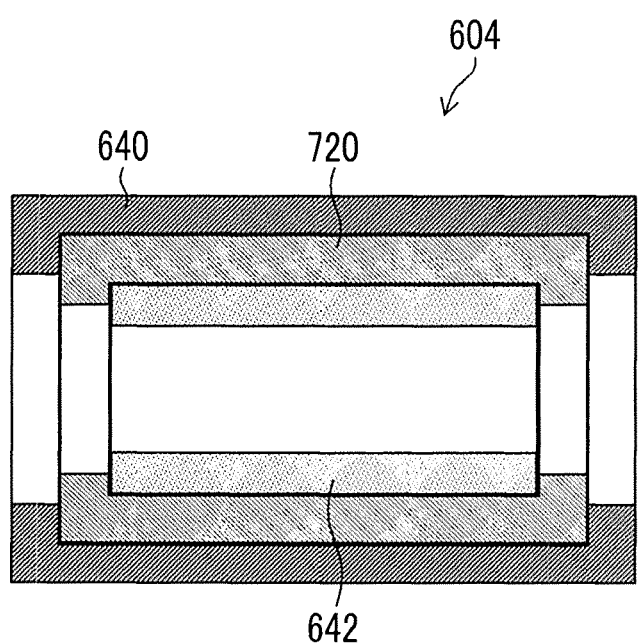
FIG. 25 is a view illustrating another embodiment of a second sleeve in the interlocking member of the embodiment of the invention.

In addition, the first sleeve 602 may be configured similar to the second sleeve 604 of FIG. 25.

Additionally, in the overtube 300 of the above embodiment, the reference axis 300a, the endoscope insertion axis 306a, and the treatment tool insertion axis 308a are parallel to each other. However, at least one of the endoscope insertion axis 306a and the treatment tool insertion axis 308a may be inclined (non-parallel) with respect to the reference axis 300a.

For example, in a case where a plane including the reference axis 300a having a normal line in the upward-downward direction is referred to as a horizontal reference plane and a plane including the reference axis 300a and having a normal line in the leftward-rightward direction is referred to as a vertical reference plane, the reference axis 300a, the endoscope insertion axis 306a and the treatment tool insertion axis 308a are all parallel to each other on the horizontal reference plane in a case where the endoscope insertion axis 306a and the treatment tool insertion axis 308a are projected on the horizontal reference plane. And although the reference axis 300a and the treatment tool insertion axis 308a are parallel to each other on the vertical reference plane in a case where the endoscope insertion axis 306a and the treatment tool insertion axis 308a are projected on the vertical reference plane, a form may be adopted in which the reference axis 300a and the endoscope insertion axis 306a are not parallel to each other and the endoscope insertion axis 306a is inclined obliquely, for example, toward a front upper side from a rear lower side.

Accordingly, the overtube 300 guides the endoscope insertion part 102 in an oblique direction with respect to a guiding direction of the treatment tool insertion part 202, and increases the spacing between the observation part (observation window 116) of the distal end of the endoscope insertion part 102 and the treatment part 206 of the distal end of the treatment tool insertion part 202 in order to prevent a distal end portion of the treatment part 206 of the distal end of the treatment tool insertion part 202 from becoming a dead area so that the distal end of the treatment part 206 can be visually recognized on an observation image.

EXPLANATION OF REFERENCES

10: endoscopic surgical device
100: endoscope
102: endoscope insertion part
104: cable part
108: processor device
110: light source device
112: monitor
116: observation window
118: illumination window
200: treatment tool
202: treatment tool insertion part
204: operating part
206: treatment part
300: overtube
300a: reference axis
302: proximal end surface
304: distal end surface
306: endoscope insertion passage
306a: endoscope insertion axis
308: treatment tool insertion passage
308a: treatment tool insertion axis
310: first proximal end opening
312: first distal end opening
314: second proximal end opening
316: second distal end opening
320: long tubular overtube body
322: outer wall
324: cavity part
340: proximal end cap
342, 344: through-hole
346, 348: valve member
360: distal end cap
362, 364: through-hole
370, 372: guide groove
374, 376: guide plate
400: slider
402: slider body
404: upper surface
406: lower surface
408, 410: protruding strip
420: endoscope coupling part
422: treatment tool coupling part
424: through-hole
426: pressure-contact member
430: opening
431: left side surface
440: sleeve
444: sleeve body
446: pressure-contact member
450: through-hole
460: guide part
462: guide surface
466, 468: end edge part
600: interlocking member
602: first sleeve
602a: through-hole
604: second sleeve
604a: through-hole
606: coupling member
606a: first end part
606b: second end part
620, 640: sleeve body
622, 642: pressure-contact member
660, 662, 664, 666, 668, 670: guide plate
672, 674, 676, 678: guide groove
680, 682, 684, 686: protruding strip
702: support part
710: coupling member
710a: first end part
710b: second end part
720: intermediate frame

What is claimed is:

1. An endoscopic surgical device comprising:
a first medical instrument having a first insertion part;
a second medical instrument having a second insertion part;
a tubular overtube allowing the first insertion part and the second insertion part to be inserted therethrough and guiding the first insertion part and the second insertion part into a body cavity;
a first sleeve that is disposed inside the overtube, holds the first insertion part inserted through the inside of the overtube, and moves in an axial direction of the overtube in a state where the first insertion part is held;
a second sleeve that is disposed inside the overtube, holds the second insertion part inserted through the inside of the overtube, and moves in the axial direction of the overtube in a state where the second insertion part is held, wherein the first and second sleeves are separate structures;
a coupling member which has a first end fixed to an outer surface of the first sleeve and a second end fixed to an outer surface of the second sleeve, and has an elastic body between the first end and the second end; and
a resistance force generating part that generates a resistance force which hinders the movement of the first sleeve in the axial direction of the overtube.

2. The endoscopic surgical device according to claim 1, wherein, a length of the elastic body when no load is applied to the elastic body is referred to as a natural length, in a case where a distance between the first end and the second end of the coupling member when no load is applied to the elastic body is defined as the natural length L1 and a distance between the first end and the second end when the second end has moved relative to the overtube is defined as L2, the coupling member generates a force biasing the first end and the second end in directions along the axial direction of the overtube that brings the first end and the second end closer to each other, in a case where the distance L2 becomes longer than L1.

3. The endoscopic surgical device according to claim 2, wherein, in the coupling member, the force biasing the first end and the second end in the directions along the axial direction of the overtube that brings the ends closer to each other increases as the distance of L2 becomes longer than L1.

4. The endoscopic surgical device according to claim 1, wherein, a length of the elastic body when no load is applied to the elastic body is referred to as a natural length, in a case where a distance between the first end and the second end of the coupling member when no load is applied to the elastic body is defined as the natural length L1 and a distance between the first end and the second end when the second end has moved relative to the overtube is defined as L2, the coupling member generates a force biasing the first end and the second end in directions along the axial direction of the overtube that moves the first end and the second end away from each other, in a case where the distance L2 becomes shorter than L1.

5. The endoscopic surgical device according to claim 4, wherein, in the coupling member, the force biasing the first end and the second end in the directions along the axial direction of the overtube that moves the first end and the second end away from each other increases as the distance of L2 becomes shorter than L1.

6. The endoscopic surgical device according to claim 1, wherein the resistance force generating part is provided between the first sleeve and the overtube.

7. The endoscopic surgical device according to claim 1, wherein the resistance force generating part is provided between the first insertion part and the overtube.

8. The endoscopic surgical device according to claim 7, wherein the overtube has a valve member that secures the airtightness in an internal space of the overtube by being in contact with the first insertion part, and wherein the resistance force generating part comprises the valve member.

9. The endoscopic surgical device according to claim 1, wherein the first medical instrument is an endoscope in which an observation part is provided at a distal end of the first insertion part, and wherein the second medical instrument is a treatment tool in which a treatment part is provided at a distal end of the second insertion part.

10. A guide device comprising:
a tubular overtube allowing a first insertion part of a first medical instrument and a second insertion part of a second medical instrument to be inserted therethrough and guiding the first insertion part and the second insertion part into a body cavity;
a first sleeve that is disposed inside the overtube, holds the first insertion part inserted through the inside of the overtube, and moves in an axial direction of the overtube in a state where the first insertion part is held;
a second sleeve that is disposed inside the overtube, holds the second insertion part inserted through the inside of the overtube, and moves in the axial direction of the overtube in a state where the second insertion part is held, wherein the first and second sleeves are separate structures;
a coupling member which has a first end fixed to an outer surface of the first sleeve and a second end fixed to an outer surface of the second sleeve, and has an elastic body between the first end and the second end; and
a resistance force generating part that generates a resistance force which hinders the movement of the first sleeve in the axial direction of the overtube.

11. The guide device according to claim 10, wherein, a length of the elastic body when no load is applied to the elastic body is referred to as a natural length, in a case where a distance between the first end and the second end of the coupling member when no load is applied to the elastic body is defined as the natural length L1 and a distance between the first end and the second end when the second end has moved relative to the overtube is defined as L2, the coupling member generates a force biasing the first end and the second end in directions along the axial direction of the overtube that brings the first end and the second end closer to each other, in a case where the distance L2 becomes longer than L1.

12. The guide device according to claim 11, wherein, in the coupling member, the force biasing the first end and the second end in the directions along the axial direction of the overtube that brings the ends closer to each other increases as the distance of L2 becomes longer than L1.

13. The guide device according to claim 10, wherein, a length of the elastic body when no load is applied to the elastic body is referred to as a natural length, in a case where a distance between the first end and the second end of the coupling member when no load is applied to the elastic body is defined as the natural length L1 and a distance between the first end and the second end when the second end has moved relative to the overtube is defined as L2, the coupling member generates a force biasing the first end and the second end in directions along the axial direction of the overtube that moves the first end and the second end away from each other, in a case where the distance L2 becomes shorter than L1.

14. The guide device according to claim 13, wherein, in the coupling member, the force biasing the first end and the second end in the directions along the axial direction of the overtube that moves the first end and the second end away from each other increases as the distance of L2 becomes shorter than L1.

15. The guide device according to claim 10, wherein the resistance force generating part is provided between the first sleeve and the overtube.

16. The guide device according to claim 10, wherein the resistance force generating part is provided between the first insertion part and the overtube.

17. The guide device according to claim 16, wherein the overtube has a valve member that secures the airtightness in an internal space of the overtube by being in contact with the first insertion part, and wherein the resistance force generating part comprises the valve member.

18. An endoscopic surgical device comprising:
a first medical instrument having a first insertion part;
a second medical instrument having a second insertion part;
a tubular overtube allowing the first insertion part and the second insertion part to be inserted therethrough and guiding the first insertion part and the second insertion part into a body cavity;
a first sleeve that is disposed inside the overtube, holds the first insertion part inserted through the inside of the overtube, and moves in an axial direction of the overtube in a state where the first insertion part is held;
a second sleeve that is disposed inside the overtube, holds the second insertion part inserted through the inside of the overtube, and moves in the axial direction of the overtube in a state where the second insertion part is held;
a coupling member which has a first end fixed to an outer surface of the first sleeve and a second end fixed to an outer surface of the second sleeve, and has an elastic body between the first end and the second end; and
a resistance force generating part that generates a resistance force which hinders the movement of the first sleeve in the axial direction of the overtube,
wherein, a length of the elastic body when no load is applied to the elastic body is referred to as a natural length, in a case where a distance between the first end and the second end of the coupling member when no load is applied to the elastic body is defined as the natural length $L1$ and a distance between the first end and the second end when the second end has moved relative to the overtube is defined as $L2$, the coupling member generates a force biasing the first end and the second end in directions along the axial direction of the overtube that brings the first end and the second end closer to each other, in a case where the distance $L2$ becomes longer than $L1$,
wherein, in the coupling member, the force biasing the first end and the second end in the directions along the axial direction of the overtube that brings the ends closer to each other increases as the distance of $L2$ becomes longer than $L1$,
wherein the resistance force generating part is provided between the first insertion part and the overtube,
wherein the overtube has a valve member that secures the airtightness in an internal space of the overtube by being in contact with the first insertion part,
wherein the resistance force generating part comprises the valve member, and the valve member is disposed inside a proximal end cap provided at a proximal end of the overtube,
wherein the first medical instrument is an endoscope in which an observation part is provided at a distal end of the first insertion part, and
wherein the second medical instrument is a treatment tool in which a treatment part is provided at a distal end of the second insertion part.

* * * * *